(12) United States Patent
Olschewski et al.

(10) Patent No.: US 9,339,507 B2
(45) Date of Patent: May 17, 2016

(54) TREPROSTINIL ADMINISTRATION BY INHALATION

(75) Inventors: Horst Olschewski, Graz (AT); Robert Roscigno, Chapel Hill, NC (US); Lewis J. Rubin, LaJolla, CA (US); Thomas Schmehl, Giessen (DE); Werner Seeger, Giessen (DE); Carl Sterritt, Weybridge (GB); Robert Voswinckel, Giessen (DE)

(73) Assignee: United Therapeutics Corporation, Silver Spring, MD (US)

( * ) Notice: Subject to any disclaimer, the term of this patent is extended or adjusted under 35 U.S.C. 154(b) by 301 days.

(21) Appl. No.: 13/469,854

(22) Filed: May 11, 2012

(65) Prior Publication Data

US 2012/0216801 A1    Aug. 30, 2012

Related U.S. Application Data

(60) Division of application No. 12/591,200, filed on Nov. 12, 2009, which is a continuation of application No. 11/748,205, filed on May 14, 2007.

(60) Provisional application No. 60/800,016, filed on May 15, 2006.

(51) Int. Cl.
| | | |
|---|---|---|
| *A61K 31/192* | (2006.01) | |
| *A61P 9/12* | (2006.01) | |
| *A61M 11/00* | (2006.01) | |
| *A61K 31/557* | (2006.01) | |
| *A61K 9/00* | (2006.01) | |

(52) U.S. Cl.
CPC ............... *A61K 31/557* (2013.01); *A61K 9/008* (2013.01); *A61K 9/0078* (2013.01)

(58) Field of Classification Search
CPC ............................. A61K 31/557; A61K 9/008
USPC ........................................................ 514/569
See application file for complete search history.

(56) References Cited

U.S. PATENT DOCUMENTS

| | | |
|---|---|---|
| 3,664,337 A | 5/1972 | Lindsey et al. |
| 4,001,650 A | 1/1977 | Romain |
| 4,281,113 A | 7/1981 | Axen et al. |
| 4,306,075 A | 12/1981 | Aristoff |
| 4,306,076 A | 12/1981 | Nelson |
| 4,349,689 A | 9/1982 | Aristoff |
| 4,473,296 A | 9/1984 | Shofner et al. |
| 4,486,598 A | 12/1984 | Aristoff |
| 4,495,944 A | 1/1985 | Brisson et al. |
| 4,635,647 A | 1/1987 | Choksi |
| 4,668,814 A | 5/1987 | Aristoff |
| 4,677,975 A | 7/1987 | Edgar et al. |
| 4,683,330 A | 7/1987 | Aristoff |
| 4,692,464 A | 9/1987 | Skuballa et al. |
| 4,708,963 A | 11/1987 | Skuballa et al. |
| 4,976,259 A | 12/1990 | Higson et al. |
| 4,984,158 A | 1/1991 | Hillsman |
| 5,063,922 A | 11/1991 | Hakkinen |
| 5,080,093 A | 1/1992 | Raabe et al. |
| 5,153,222 A | 10/1992 | Tadepalli et al. |
| 5,234,953 A | 8/1993 | Crow et al. |
| 5,322,057 A | 6/1994 | Raabe et al. |
| 5,361,989 A | 11/1994 | Merchat et al. |
| 5,363,842 A | 11/1994 | Mishelevich et al. |
| 5,497,763 A | 3/1996 | Lloyd et al. |
| 5,551,416 A | 9/1996 | Stimpson et al. |
| 5,727,542 A | 3/1998 | King |
| 5,865,171 A | 2/1999 | Cinquin |
| 5,881,715 A | 3/1999 | Shibasaki |
| 5,908,158 A | 6/1999 | Cheiman |
| 6,054,486 A | 4/2000 | Crow et al. |
| 6,123,068 A | 9/2000 | Lloyd et al. |
| 6,357,671 B1 | 3/2002 | Cewers |
| 6,521,212 B1 | 2/2003 | Cloutier et al. |
| 6,626,843 B2 | 9/2003 | Hillsman |
| 6,756,033 B2 | 6/2004 | Cloutier et al. |
| 6,765,117 B2 | 7/2004 | Moriarty et al. |
| 6,803,386 B2 | 10/2004 | Shorr et al. |
| 6,809,223 B2 | 10/2004 | Moriarty et al. |
| 7,172,557 B1 | 2/2007 | Parker |
| 7,199,157 B2 | 4/2007 | Wade et al. |
| 7,384,978 B2 | 6/2008 | Phares et al. |
| 7,417,070 B2 | 8/2008 | Phares et al. |
| 7,544,713 B2 | 6/2009 | Phares et al. |
| 7,726,303 B2 | 6/2010 | Tyvoll et al. |
| 2003/0192532 A1 | 10/2003 | Hopkins |
| 2004/0063912 A1 | 4/2004 | Blumberg et al. |
| 2004/0105819 A1 | 6/2004 | Hale et al. |
| 2004/0149282 A1 | 8/2004 | Hickle |
| 2004/0265238 A1 | 12/2004 | Chaudry |
| 2005/0165111 A1 | 7/2005 | Wade et al. |
| 2005/0166913 A1 | 8/2005 | Sexton et al. |
| 2005/0183719 A1 | 8/2005 | Wuttke et al. |

(Continued)

FOREIGN PATENT DOCUMENTS

| | | |
|---|---|---|
| AU | 1999959533 B2 | 2/2000 |
| DE | 19838711 C1 | 6/2000 |

(Continued)

OTHER PUBLICATIONS

EPA Integrated Risk Information System (IRIS): data sheet for 3-methylphenol (m-cresol). Accessed at http://www.epa.gov/iris/subst/0301.htm on Mar. 9, 2014.*

(Continued)

*Primary Examiner* — Jeffrey S Lundgren
*Assistant Examiner* — Sara E Townsley
(74) *Attorney, Agent, or Firm* — Foley & Lardner LLP

(57) ABSTRACT

Treprostinil can be administered using a metered dose inhaler. Such administration provides a greater degree of autonomy to patients. Also disclosed are kits that include a metered dose inhaler containing a pharmaceutical formulation containing treprostinil.

9 Claims, 12 Drawing Sheets

(56) References Cited

U.S. PATENT DOCUMENTS

| | | |
|---|---|---|
| 2005/0282901 A1 | 12/2005 | Phares et al. |
| 2006/0147520 A1 | 7/2006 | Ruegg |
| 2006/0201500 A1 | 9/2006 | Von Hollen et al. |
| 2008/0200449 A1 | 8/2008 | Olschewski et al. |
| 2008/0280986 A1 | 11/2008 | Wade et al. |
| 2009/0036465 A1 | 2/2009 | Roscigno et al. |
| 2010/0076083 A1 | 3/2010 | Olschewski et al. |
| 2010/0236545 A1 | 9/2010 | Kern |
| 2010/0282622 A1 | 11/2010 | Phares |
| 2012/0177693 A1 | 7/2012 | Cipolla et al. |

FOREIGN PATENT DOCUMENTS

| | | |
|---|---|---|
| DE | 19934582 A1 | 1/2001 |
| FR | 2783431 A1 | 3/2000 |
| JP | 2003-522003 A | 7/2003 |
| WO | WO 01/58514 A1 | 8/2001 |
| WO | WO 01/85241 A1 | 11/2001 |

OTHER PUBLICATIONS

Abe et al., "Effects of inhaled prostacyclin analogue on chronic hypoxic pulmonary hypertension," J. Cardiovascular Pharmacology, 2001, 37, 239 251.

Aradigm Corporation news release Oct. 24, 2005, "Aradigm and United Therapeutics Sign Development and Commercialization Agreement Targeting Pulmonary Hypertension," Red Orbit News, http://www.redorbit.com/modules/news/tools.php?tool=print&id=281787, 2 pages.

Aristoff et al., "Synthesis of benzopyran prostaglandins, potent stable prostacyclin analogs, via an intermolecular mitsunobu reaction," Tetrahedron Letters, 1984, 25(36):3955-3958.

Bein et al., "Cardiovascular and pulmonary effects of aerosolized prostacyclin andministration in severe respiratory failure using a ventilator nebulization system," J. Cardiovascular Pharmacology, 1996, 27, 583-586.

Benedict et al., "Evidence-based pharmacologic management of pulmonary arterial hypertension," Clinical Therapeutics, 2007, 29, 2134-2153.

Bindl et al., "Aerosolised porstacyclin for pulmonary hypertension in neonates," Archives of disease in childhood, Fetal and neonatal edition, 1994, 71(3), F214-6.

Booke et al., "Prostaglandins in Patients with Pulmonary Hypertension: The Route of Administration," Anesth. Analg., 1998, 86:917, Letter to the Editor.

Byron, Peter R., "Drug Delivery Devices, Issues in Drug Development," Proc. Am. Thorac. Soc., 2004, 1:321-328.

Channick et al., "Safety and efficacy of inhaled treprostinil as add-on therapy to bosentan in pulmonary arterial hypertension," J. American College of Cardiology, 2006, 48, 1433-1437.

Doyle et al., "Inhaled prostacyclin as a selective pulmonary vasodilator," Anaesthesia and Intensive Care, Aug. 1996, 24(4):514-515.

Dumas et al,. "Hypoxic pulmonary vasoconstriction," General Pharmacology, 1999, 33, 289-297.

Dworetz et al., "Survival of infants with persistent pulmonary hypertension without extracorporeal membrane oxygenation," Pediatrics, 1989, 84, 1-6.

Ewert et al., "Aerosolized iloprost for primary pulmonary hypertension," New England Journal of Medicine, 2000, 343, 1421-1422.

Ewert et al., "Iloprost als inhalative bzw. Intravenose langzeitbehandlung von patienten mit primarer pulmonaler hypertonie," Z. Kardiol., 2000, 89, 987-999.

Fink et al., "Use of Prostacyclin and its Analogues in the Treatment of Cardiovascular Disease," Heart Disease, 1999, 1:29-40.

Gessler et al., "Ultrasonic versus jet nebulization of iloprost in severe pulmonary hypertention," Eur. Respir. J., 2001, 17, 14-19.

Ghofrani et al., "Hypoxia- and non-hypoxia-related pulmonary hypertension—Established and new therapies," Cardiovascular Research, 2006, 72:30-40.

Haraldsson et al., "Comparison of inhaled nitric oxide and inhaled aerosolized prostacyclin in the evaluation of heart transplant candidates with elevated pulmonary vascular resistance," Chest, 1998, 114, 780-786.

Hoeper et al., "A comparison of the acute hemodynamic effects of inhaled nitric oxide and aerosolized iloprost in primary hypertension," J. American College of Cardiology, 2000, 35, 176-182.

Hoeper et al., "Effects of inhaled nitric oxide and aerosolized iloprost in pulmonary veno-occlusive disease," Respiratory Medicine, 1999, 93, 62-70.

Hoeper et al., "Long term treatment of primary pulmonary hypertension with aerosolized iloprost, a prostacyclin analogue," New England Journal of Medicine, 2000, 342, 1866-1870.

Howarth, P.H., "Why particle size should affect clinical response to inhaled therapy," Journal of Aerosol Medicine, 2001, 14 Supp. 1, S-27-S-34.

Ichida et al., "Additive effects of beraprost on pulmonary vasodilation by inhaled nitric oxide in children with pulmonary hypertension," American Journal of Cardiology, 1997, 80, 662-664.

Krause et al., "Pharmacokinetics and pharmacodynamics of the prostacyclin analogue iloprost in man," Eur. J. Clin. Pharmacol., 1986, 30, 61-68.

Lee et al., "Current strategies for pulmonary arterial hypertension," J. Internal Medicine, 2005, 258, 199-215.

Martin, John C., "Inhaled Form of Remodulin in the Pipeline," http://www.phneighborhood.com/content/in_the_news/archive_2320.aspx, ph Neighborhood, Oct. 28, 2005, 2 pages.

Max et al., "Inhaled prostacylin in the treatment of pulmonary hypertension," Eur. J. Pediatr., 1999, 158 Suppl 1, S23-S26.

Nebu-Tec med. Produkte Eike Kern GmbH, VENTA-NEB®-ir A-I-C-I® Operating Instrutions, Sep. 2005.

Olschewski et al. for the German PPH Study Group, "Inhaled iloprost to treat severe pulmonary hypertension—An uncontrolled trial," Annals of Internal Medicine, 2000, 132, 435-443.

Olschewski et al., Aerosolized prostacyclin and iloprost in severe pulmonary hypertension,: Annals of Internal Medicine, 1996, 124, 820 824.

Olschewski et al., "Inhaled prostacyclin and iloprost in severe pulmonary hypertension secondary to lung fibrosis," Am. Respir. Crit. Care Med., 1999, 160, 600-607.

Olschewski et al., "Pharmacodynamics and pharmacokinetics of inhaled iloprost, aerosolized by three different devices, in severe pulmonary hypertension," Chest, 2003, 124, 1294-1304.

Olschewski et al., "Prostacyclin and its analogues in the treatment of pulmonary hypertension," Pharmacology and Therapeutics, 2004, 102, 139-153.

Olschewski et al., "Recovery from circulatory shock in severe primary pulmonary hypertension (PPH) with aerosolization of iloprost," Intensive Care Med., 1998, 24, 631-634.

Pappert et al., "Aerosolized Prostacyclin Versus Inhaled Nitric Oxide in Children with Severe Acute Respiratory Distress Syndrome," Anesthesiology, Jun. 1995, 82(6):1507-1511.

Rigby, Jonathan, Aradigm Corporation, "Technological advances for success: Product pipeline in targeted pulmonary delivery," Pulmonary Delivery Innovative Technologies Breathing New Life into Inhalable Therapeutics, ONdrugDelivery, http://www.ondrugdelivery.com/publications/Pulmonary.pdf, 2006, 17-19.

Sandifer et al., "Potent effects of aerosol compared with intravenous treprostinil on the pulmonary circulation," J. Appl. Physiol., 2005, 99:2363-2368.

Santak et al., "Prostacyclin aerosol in an infant with pulmonary hypertension," Eur. J. Pediatr., 1995, 154, 233-235.

Soditt et al., "Improvement of oxygenation induced by aerosolized prostacyclin in a preterm infant with persistent pulmonary hypertension of the newborn," Intensive Care Med., 1997, 23, 1275-1278.

Steffen et al., "The Effects of 15AU81, a Chemically Stable Prostacyclin Analog, on the Cardiovascular and Renin-Angiotensis Systems of Anesthetized Dogs," Prostaglandins, Leukotrienes and Essential Fatty Acids, 1991, 43:277-286.

Stricker et al., "Sustained improvement of performance and haemodynamics with long-term aerosolized prostacyclin therapy in severe pulmonary hypertension," Schweiz Med. Wochenschr., 1999, 129, 923-927.

(56) References Cited

OTHER PUBLICATIONS

Van Heerden et al., "Inhaled aerosolized prostacyclin as a selective pulmonary vasodilator for the treatment of severe hypertension," Anaesthesia and Intensive Care, 1996, 24, 87-90.
Van Heerden et al., "Re: Delivery of inhaled aerosolized prostacyclin (IAP)," Anaesthesia and Intensive Care, 1996, 24, 624-625.
Voswinckel et al., "Acute effects of the combination of sildenafil and inhaled treprostinil on haemodynamics and gas exchange in pulmonary hypertension," Pulmonary Pharmacology & Therapeutics, 2008, 21, 824-832.
Voswinckel et al., "Favorable Effects of Inhaled Treprostinil in Severe Pulmonary Hypertension," Journal of the American College of Cardiology, 2006, 48(8):1672-1681.
Voswinckel et al., "Inhaled Treprostinil for Treatment of Chronic Pulmonary Arterial Hypertension," Annals of Internal Medicine, Jan. 17, 2006, 144(2):149-150.
Walmrath et al., "Effects of inhaled versus intravenous vasodilators in experimental pulmonary hypertension," Eur. Respir. J., 1997, 10, 1084-1092.
Wasserman et al., "Bronchodilator effects of prostacyclin (PGI2) in dogs and guinea pigs," European Journal of Pharmacology, 1980, 66, 53-63.
Webb et al., "The use of inhaled aerosolized prostacyclin (IAP) in the treatment of pulmonary hypertension secondary to pulmonary embolism," Intensive Care Med., 1996, 22, 353-355.
Wensel et al., "Effects of iloprost inhalation on exercise capacity and ventilator efficiency in patients with primary pulmonary hypertension," Circulation, 2000, 101, 2388-2392.
Wetzel, R.C., "Aerosolized prostacyclin: in search of the ideal pulmonary vasodilator," Anesthesiology, 1995, 82, 1315-1317.
Zanen et al., "Optimal particle size for beta 2 agonist and anticholinergic aerosols in patients with severe airflow obstruction," Thorax, 1996, 51, 977-980.
Zanen et al., "The optimal particle size for β-adrenergic aerosols in mild asthmatics," International Journal of Pharmaceutics, 1994, 107, 211-217.
Findlay et al., "Radioimmunoassay for the Chemical Stable Prostacyclin Analog, 15AU81: a Preliminary Pharmacokinetics Study in the Dog," Prostaglandins Leukot. Essent. Fatty Acids, Feb. 1993, 48(2):167-174.
McNulty et al., "The Pharmacokinetics and Pharmacodynamics of the Prostacyclin Analog 15AU81 in the Anesthetized Beagle Dog," Prostaglandins Leukot. Essent. Fatty Acids, Feb. 1993, 48(2):159-166.
Saini et al., "Effect of Electrostatic Charge and Size Distributions on Respirable Aerosol Deposition in Lung Model," Industry Applications Conference, 2004, 39th IAS Annual Meeting, Conference Record of the 2004 IEEE Seattle, WA, Oct. 3-7, 2004, 2:948-952.
Wittwer et al., "Inhalative Pre-Treatment of Donor Lungs Using the Aerosolized Prostacyclin Analog Iloprost Ameliorates Reperfusion Injury," J. Heart Lung Transplant, 2005, 24:1673-1679.
Agnew JE, Bateman RM, Pavia D, Clarke SW. (1984) Radionuclide demonstration of ventilatory abnormalities in mild asthma. Clinical Science; 66: 525-531.
Annals of the International Commission on Radiological Protection (ICRP) vol. 28, No. 3, 1998, Publication 80, Radiation Dose to Patients from Radiopharmaceuticals.
Blanchard, J.D., Cipolla, D., Liu, K., Morishige, R., Mudumba, S., Thipphawong, J., Taylor, G., Warren, S., Radhakrishnan, R., Van Vlasselaer, R., Visor, G. and Starko, K. (2003) Lung Deposition of Interferon Gamma-1b following Inhalation via AERx® System vs. Respirgard II™ Nebulizer Proc. ATS Annual Meeting (Abstract A373), Seattle.
Boyd, B., Noymer, P., Liu, K., Okikawa, J., Hasegawa, D., Warren, S., Taylor, G., Ferguson, E., Schuster, J., Farr, S., and Gonda, I. (2004) Effect of Gender and Device Mouthpiece Shape on Bolus Insulin Aerosol Delivery Using the AERx Pulmonary Delivery System. Pharmaceutical Research. 21 (10) 1776-1782.
Colthorpe P, Taylor G, Farr SJ. (1997) A comparison of two non-invasive methods for quantifying aerosol deposition in the lungs of rabbits. J. Aerosol Med.; 10:255.
Farr et al., "Comparison of in vitro and in vivo efficiencies of a novel unit-dose liquid aerosol generator and a pressurized metered dose inhaler," International Journal of Pharmaceutics, 2000, 198:63-70.
Miller et al., "Standardisation of spirometry. Series ATS/ERS Task Force: Standardisation of Lung Function Testing" Eur Respir J 2005; 26: 319-338.
National Radiological Protection Board. Doses to Patients from Medical Radiological Examinations in Great Britain. (1986) Radiological Protection Bulletin No. 77.
Notes for Guidance on the Clinical Administration of Radiopharmaceuticals and Use of Sealed Radioactive Sources. Administration of Radioactive Substances Advisory Committee (ARSAC) (Mar. 2006). ARSAC Secretariat, Chilton, Didcot, Oxon. OX11 0RQ.
Publications of the International Commission on Radiological Protection (ICRP) (1977) Recommendations of the International Commission on Radiological Protection 26.
Pulmonary Delivery, ONdrugDelivery, 2006, 5 pages.
Final Office Action dated Oct. 10, 2014 in U.S. Appl. No. 12/591,200.
Non-Final Office Action dated Mar. 9, 2014 in U.S. Appl. No. 12/591,200.
Final Office Action dated Oct. 17, 2012 in U.S. Appl. No. 12/591,200.
Final Office Action dated Dec. 22, 2011 in U.S. Appl. No. 12/591,200.
Non-Final Office Action dated Jan. 29, 2015 in U.S. Appl. No. 13/120,015.
Final Office Action dated Jul. 2, 2013 in U.S. Appl. No. 13/120,015.
Non-Final Office Action dated Oct. 31, 2012 in U.S. Appl. No. 13/120,015.
Non-Final Office Action dated Dec. 30, 2014 in U.S. Appl. No. 12/303,877.
Final Office Action dated Nov. 4, 2013 in U.S. Appl. No. 12/303,877.
Non-Final Office Action dated Mar. 15, 2013 in U.S. Appl. No. 12/303,877.
Final Office Action dated Aug. 1, 2012 in U.S. Appl. No. 12/303,877.
Non-Final Office Action dated Oct. 11, 2011 in U.S. Appl. No. 12/303,877.
Scientific discussion for the approval of Ventavis, European Medicines Agency (EMEA), Oct. 20, 2004, 30 pages.

* cited by examiner

TREPROSTINIL ADMINISTRATION BY INHALATION

CROSS REFERENCE TO RELATED APPLICATIONS

The present application is a Divisional of U.S. application Ser. No. 12/591,200, filed Nov. 12, 2009, which is a Continuation of U.S. application Ser. No. 11/748,205, filed May 14, 2007, which claims priority to U.S. provisional application No. 60/800,016 filed May 15, 2006, which are incorporated herein by reference in their entirety.

FIELD OF THE INVENTION

The present application relates to methods and kits for therapeutic treatment and, more particularly, to therapeutic methods involving administering treprostinil using a metered dose inhaler and related kits.

BACKGROUND OF THE INVENTION

All blood is driven through the lungs via the pulmonary circulation in order, among other things, to replenish the oxygen which it dispenses in its passage around the rest of the body via the systemic circulation. The flow through both circulations is in normal circumstances equal, but the resistance offered to it in the pulmonary circulation is generally much less than that of the systemic circulation. When the resistance to pulmonary blood flow increases, the pressure in the circulation is greater for any particular flow. The above described condition is referred to as pulmonary hypertension (PH). Generally, pulmonary hypertension is defined through observations of pressures above the normal range pertaining in the majority of people residing at the same altitude and engaged in similar activities.

Pulmonary hypertension may occur due to various reasons and the different entities of pulmonary hypertension were classified based on clinical and pathological grounds in 5 categories according to the latest WHO convention, see e.g. Simonneau G., et al. J. Am. Coll. Cardiol. 2004; 43(12 Suppl S):5S-12S. Pulmonary hypertension can be a manifestation of an obvious or explicable increase in resistance, such as obstruction to blood flow by pulmonary emboli, malfunction of the heart's valves or muscle in handling blood after its passage through the lungs, diminution in pulmonary vessel caliber as a reflex response to alveolar hypoxia due to lung diseases or high altitude, or a mismatch of vascular capacity and essential blood flow, such as shunting of blood in congenital abnormalities or surgical removal of lung tissue. In addition, certain infectious diseases, such as HIV and liver diseases with portal hypertension may cause pulmonary hypertension. Autoimmune disorders, such as collagen vascular diseases, also often lead to pulmonary vascular narrowing and contribute to a significant number of pulmonary hypertension patients. The cases of pulmonary hypertension remain where the cause of the increased resistance is as yet inexplicable are defined as idiopathic (primary) pulmonary hypertension (iPAH) and are diagnosed by and after exclusion of the causes of secondary pulmonary hypertension and are in the majority of cases related to a genetic mutation in the bone morphogenetic protein receptor-2 gene. The cases of idiopathic pulmonary arterial hypertension tend to comprise a recognizable entity of about 40% of patients cared for in large specialized pulmonary hypertension centers. Approximately 65% of the most commonly afflicted are female and young adults, though it has occurred in children and patients over 50. Life expectancy from the time of diagnosis is short without specific treatment, about 3 to 5 years, though occasional reports of spontaneous remission and longer survival are to be expected given the nature of the diagnostic process. Generally, however, disease progress is inexorable via syncope and right heart failure and death is quite often sudden.

Pulmonary hypertension refers to a condition associated with an elevation of pulmonary arterial pressure (PAP) over normal levels. In humans, a typical mean PAP is approximately 12-15 mm Hg. Pulmonary hypertension, on the other hand, can be defined as mean PAP above 25 mmHg, assessed by right heart catheter measurement. Pulmonary arterial pressure may reach systemic pressure levels or even exceed these in severe forms of pulmonary hypertension. When the PAP markedly increases due to pulmonary venous congestion, i.e. in left heart failure or valve dysfunction, plasma can escape from the capillaries into the lung interstitium and alveoli. Fluid buildup in the lung (pulmonary edema) can result, with an associated decrease in lung function that can in some cases be fatal. Pulmonary edema, however, is not a feature of even severe pulmonary hypertension due to pulmonary vascular changes in all other entities of this disease.

Pulmonary hypertension may either be acute or chronic. Acute pulmonary hypertension is often a potentially reversible phenomenon generally attributable to constriction of the smooth muscle of the pulmonary blood vessels, which may be triggered by such conditions as hypoxia (as in high-altitude sickness), acidosis, inflammation, or pulmonary embolism. Chronic pulmonary hypertension is characterized by major structural changes in the pulmonary vasculature, which result in a decreased cross-sectional area of the pulmonary blood vessels. This may be caused by, for example, chronic hypoxia, thromboembolism, collagen vascular diseases, pulmonary hypercirculation due to left-to-right shunt, HIV infection, portal hypertension or a combination of genetic mutation and unknown causes as in idiopathic pulmonary arterial hypertension.

Pulmonary hypertension has been implicated in several life-threatening clinical conditions, such as adult respiratory distress syndrome ("ARDS") and persistent pulmonary hypertension of the newborn ("PPHN"). Zapol et al., Acute Respiratory Failure, p. 241-273, Marcel Dekker, New York (1985); Peckham, J. Ped. 93:1005 (1978). PPHN, a disorder that primarily affects full-term infants, is characterized by elevated pulmonary vascular resistance, pulmonary arterial hypertension, and right-to-left shunting of blood through the patent ductus arteriosus and foramen ovale of the newborn's heart. Mortality rates range from 12-50%. Fox, Pediatrics 59:205 (1977); Dworetz, Pediatrics 84: 1(1989). Pulmonary hypertension may also ultimately result in a potentially fatal heart condition known as "cor pulmonale," or pulmonary heart disease. Fishman, "Pulmonary Diseases and Disorders" $2^{nd}$ Ed., McGraw-Hill, New York (1988).

Currently, there is no treatment for pulmonary hypertension that can be administered using a compact inhalation device, such as a metered dose inhaler.

SUMMARY OF THE INVENTION

One embodiment is a method of delivering to a subject in need thereof a therapeutically effective amount of treprostinil, or treprostinil derivative or a pharmaceutically acceptable salt thereof comprising administering to the subject a therapeutically effective amount of the treprostinil or treprostinil derivative or a pharmaceutically acceptable salt thereof using a metered dose inhaler.

Another embodiment is a method for treating pulmonary hypertension comprising administering to a subject in need thereof treprostinil or its derivative, or a pharmaceutically acceptable salt thereof using a metered dose inhaler.

Yet another embodiment is a kit comprising a metered dose inhaler containing a pharmaceutical formulation comprising treprostinil or treprostinil derivative, or a pharmaceutically acceptable salt thereof.

And yet another embodiment is a kit for treating pulmonary hypertension in a subject, comprising (i) an effective amount of treprostinil or its derivative, or a pharmaceutically acceptable salt thereof; (ii) a metered dose inhaler; (iii) instructions for use in treating pulmonary hypertension.

Administration of treprostinil using a metered dose inhaler can provide patients, such as pulmonary hypertension patients, with a high degree of autonomy.

DETAILED DESCRIPTION OF THE INVENTION

Figure 1:
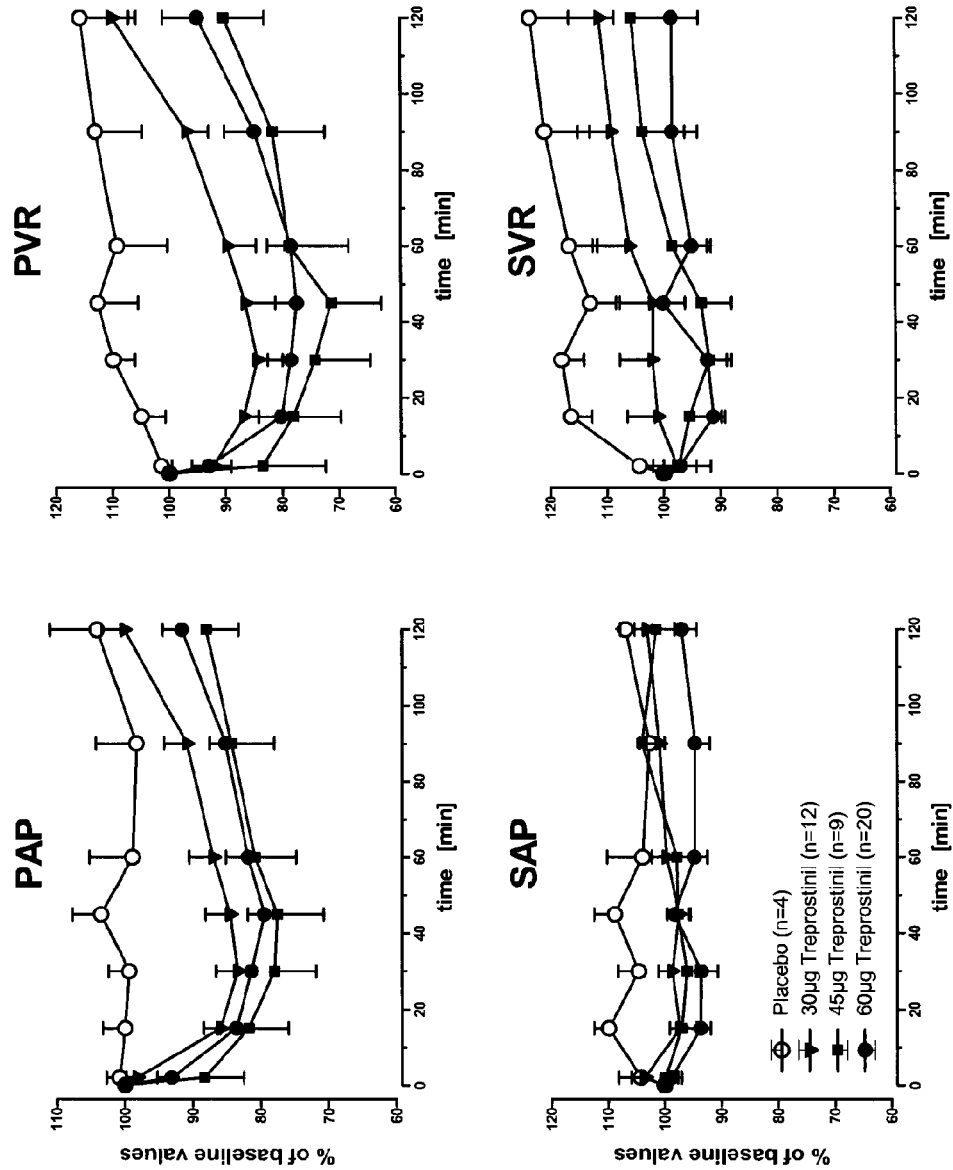
FIG. 1 pulmonary and systemic changes in hemodynamics following the inhalation of placebo (open circles), 30 µg treprostinil (triangles), 45 µg treprostinil (squares) or 60 µg TREprostinil (black circles) applied by a Metered Dose Inhaler (MDI-TRE). A single short inhalation of treprostinil induced sustained reduction of PAP and PVR that outlasted the observation period of 120 minutes at doses of 45 and 60 µg MDI-TRE. Systemic arterial pressure and resistance were not significantly affected. PAP=mean pulmonary artery pressure; PVR=pulmonary vascular resistance; SAP=mean systemic arterial pressure; SVR=systemic vascular resistance. Data are given as mean value±standard error of the mean (SEM).

Unless otherwise specified, the term "a" or "an" used herein shall mean "one or more."

The present application incorporates herein by reference in its entirety Voswinckel R, et al. J. Am. Coll. Cardiol. 2006; 48:1672-1681.

The inventors discovered that a therapeutically effective dose of treprostinil can be administered in a few single inhalations using a compact inhalation device, such as a metered dose inhaler. Furthermore, the inventors discovered that such administering does not cause significant side effects, especially no significant side effects related to systemic blood pressure and circulation as well as no gas exchange deteriorations or disruptions.

Accordingly, one embodiment of the invention is a method of delivering to a subject in need thereof, such as a human being, a therapeutically effective amount of treprostinil comprising administering to the subject a formulation comprising a therapeutically effective amount of treprostinil, its derivative or a pharmaceutically acceptable salt thereof using a metered dose inhaler. Treprostinil can be administered via a metered dose inhaler to a subject affected with a condition or disease, which can be treated by treprostinil, such as asthma, pulmonary hypertension, peripheral vascular disease or pulmonary fibrosis.

Another embodiment of the invention is a method for treating pulmonary hypertension, comprising administering to a subject in need thereof, such as a human being, treprostinil or its derivative, or a pharmaceutically acceptable salt using a metered dose inhaler.

Treprostinil, or 9-deoxy-2',9-alpha-methano-3-oxa-4,5,6-trinor-3,7-(1'3'-interphenylene)-13,14-dihydro-prostaglandin F1, is a prostacyclin analogue, first described in U.S. Pat. No. 4,306,075. U.S. Pat. No. 5,153,222 describes use of treprostinil for treatment of pulmonary hypertension. Treprostinil is approved for the intravenous as well as subcutaneous route, the latter avoiding septic events associated with continuous intravenous catheters. U.S. Pat. Nos. 6,521,212 and 6,756,033 describe administration of treprostinil by inhalation for treatment of pulmonary hypertension, peripheral vascular disease and other diseases and conditions. U.S. Pat. No. 6,803,386 discloses administration of treprostinil for treating cancer such as lung, liver, brain, pancreatic, kidney, prostate, breast, colon and head-neck cancer. US patent application publication No. 2005/0165111 discloses treprostinil treatment of ischemic lesions. U.S. Pat. No. 7,199,157 discloses that treprostinil treatment improves kidney functions. US patent application publication No. 2005/0282903 discloses treprostinil treatment of neuropathic foot ulcers. U.S. provisional application No. 60/900,320 filed Feb. 9, 2007, discloses treprostinil treatment of pulmonary fibrosis.

The term "acid derivative" is used herein to describe C1-4 alkyl esters and amides, including amides wherein the nitrogen is optionally substituted by one or two C1-4 alkyl groups.

The present invention also encompasses methods of using Treprostinil or its derivatives, or pharmaceutically acceptable salts thereof. In one embodiment, a method uses Treprostinil sodium, currently marketed under the trade name of REMODULIN®. The FDA has approved Treprostinil sodium for the treatment of pulmonary arterial hypertension by injection of dose concentrations of 1.0 mg/mL, 2.5 mg/mL, 5.0 mg/mL and 10.0 mg/mL. The chemical structure formula for Treprostinil sodium is:

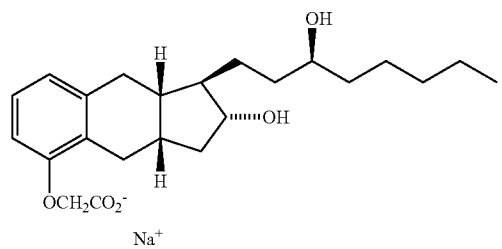

Treprostinil sodium is sometimes designated by the chemical names: (a) [(1R,2R,3aS,9aS)-2,3,3a,4,9,9a-hexahydro-2-hydroxy-1-[(3S)-3-hydroxyoctyl]-1H-benz[f]inden-5-yl]oxy]acetic acid; or (b) 9-deoxy-2',9-α-methano-3-oxa-4,5,6-trinor-3,7-(1',3'-interphenylene)-13,14-dihydro-prostaglandin $F_1$. Treprostinil sodium is also known as: UT-15; LRX-15; 15AU81; UNIPROST™; BW A15AU; and U-62,840. The molecular weight of Treprostinil sodium is 390.52, and its empirical formula is $C_{23}H_{34}O_5$.

In certain embodiments, treprostinil can be administered in combination with one or more additional active agents. In some embodiments, such one or more additional active agents can be also administered together with treprostinil using a metered dose inhaler. Yet in some embodiments, such one or more additional active agents can be administered separately from treprostinil. Particular additional active agents that can be administered in combination with treprostinil may depend on a particular disease or condition for treatment or prevention of which treprostinil is administered. In some cases, the additional active agent can be a cardiovascular agent such as a calcium channel blocker, a phosphodiesterase inhibitor, an endothelial antagonist, or an antiplatelet agent.

The present invention extends to methods of using physiologically acceptable salts of Treprostinil, as well as non-physiologically acceptable salts of Treprostinil that may be used in the preparation of the pharmacologically active compounds of the invention.

The term "pharmaceutically acceptable salt" refers to a salt of Treprostinil with an inorganic base, organic base, inorganic acid, organic acid, or basic or acidic amino acid. Salts of inorganic bases can be, for example, salts of alkali metals such as sodium or potassium; alkaline earth metals such as calcium and magnesium or aluminum; and ammonia. Salts of organic bases can be, for example, salts trimethylamine, triethylamine, pyridine, picoline, ethanolamine, diethanolamine, and triethanolamine. Salts of inorganic acids can be, for example, salts of hydrochloric acid, hydroboric acid, nitric acid, sulfuric acid, and phosphoric acid. Salts of organic acids can be, for example, salts of formic acid, acetic acid, trifluoroacetic acid, fumaric acid, oxalic acid, lactic acid, tartaric acid, maleic acid, citric acid, succinic acid, malic acid, methanesulfonic acid, benzenesulfonic acid, and p-toluenesulfonic acid. Salts of basic amino acids can be, for example, salts of arginine, lysine and ornithine. Salts of acidic amino acids can include, for example, salts of aspartic acid and glutamic acid. Quaternary ammonium salts can be formed, for example, by reaction with lower alkyl halides, such as methyl, ethyl, propyl, and butyl chlorides, bromides, and iodides, with dialkyl sulphates, with long chain halides, such as decyl, lauryl, myristyl, and stearyl chlorides, bromides, and iodides, and with aralkyl halides, such as benzyl and phenethyl bromides.

Preferred pharmaceutically acceptable salts are disclosed, for example, in US patent application publication No. 20050085540.

Treprostinil can be administered by inhalation, which in the present context refers to the delivery of the active ingredient or a combination of active ingredients through a respiratory passage, wherein the subject in need of the active ingredient(s) through the subject's airways, such as the subject's nose or mouth.

A metered dose inhaler in the present context means a device capable of delivering a metered or bolus dose of respiratory drug, such as treprostinil, to the lungs. One example of the inhalation device can be a pressurized metered dose inhaler, a device which produces the aerosol clouds for inhalation from solutions and/or suspensions of respiratory drugs in chlorofluorocarbon (CFC) and/or hydrofluoroalkane (HFA) solutions.

The inhalation device can be also a dry powder inhaler. In such case, the respiratory drug is inhaled in solid formulation, usually in the form of a powder with particle size less than 10 micrometers in diameter or less than 5 micrometers in diameter.

The metered dose inhaler can be a soft mist inhaler (SMI), in which the aerosol cloud containing a respiratory drug can be generated by passing a solution containing the respiratory drug through a nozzle or series of nozzles. The aerosol generation can be achieved in SMI, for example, by mechanical, electromechanical or thermomechanical process. Examples of soft mist inhalers include the Respimat® Inhaler (Boeringer Ingelheim GmbH), the AERx® Inhaler (Aradigm Corp.), the Mystic™ Inhaler (Ventaira Pharmaceuticals, Inc) and the Aira™ Inhaler (Chrysalis Technologies Incorporated). For a review of soft mist inhaler technology, see e.g. M. Hindle, The Drug Delivery Companies Report, Autumn/Winter 2004, pp. 31-34. The aerosol for SMI can be generated from a solution of the respiratory drug further containing pharmaceutically acceptable excipients. In the present case, the respiratory drug is treprostinil, its derivative or a pharmaceutically acceptable salt thereof, which can be formulated in SMI is as a solution. The solution can be, for example, a solution of treprostinil in water, ethanol or a mixture thereof. Preferably, the diameter of the treprostinil-containing aerosol particles is less than about 10 microns, or less than about 5 microns, or less than about 4 microns.

Treprostinil concentration in an aerosolable formulation, such as a solution, used in a metered dose inhaler can range from about 500 μg/ml to about 2500 μg/ml, or from about 800 μg/ml to about 2200 μg/ml, or from about 1000 μg/ml to about 2000 μg/ml.

The dose of treprostinil that can be administered using a metered dose inhaler in a single event can be from about 15 μg to about 100 μg or from about 15 μg to about 90 μg or from about 30 μg to about 90 μg or from about 30 μg to about 60 μg.

Administering of treprostinil in a single event can be carried out in a limited number of breaths by a patient. For example, treprostinil can be administered in 20 breaths or less, or in 10 breaths or less, or than 5 breaths or less. Preferably, treprostinil is administered in 3, 2 or 1 breaths.

The total time of a single administering event can be less than 5 minutes, or less than 1 minute, or less than 30 seconds.

Treprostinil can be administered a single time per day or several times per day.

In some embodiments, the method of treatment of pulmonary hypertension can further comprise administering at least one supplementary agent selected from the group consisting of sildenafil, tadalafil, calcium channel blockers (diltiazem, amlodipine, nifedipine), bosentan, sitaxsentan, ambrisentan, and pharmaceutically acceptable salts thereof. In some embodiments, the supplementary agents can be included in the treprostinil formulation and, thus, can be administered simultaneously with treprostinil using a metered dose inhaler. In some embodiments, the supplementary agents can be administered separately from treprostinil. In some embodiments, the application of intravenous prostacyclin (flolan), intravenous iloprost or intravenous or subcutaneous treprostinil can be administered in addition to treprostinil administered via inhalation using a metered dose inhaler.

The present invention also provides a kit that includes a metered dose inhaler containing a pharmaceutical formulation comprising treprostinil or its derivative, or a pharmaceutically acceptable salt thereof. Such a kit can further include instructions on how to use the metered dose inhaler for inhaling treprostinil. Such instructions can include, for example, information on how to coordinate patient's breathing, and actuation of the inhaler. The kit can be used by a subject, such as human being, affected with a disease or condition that can be treated by treprostinil, such as asthma, pulmonary hypertension, peripheral vascular disease or pulmonary fibrosis.

In some cases, the kit is a kit for treating pulmonary hypertension, that includes (i) a metered dose inhaler containing a pharmaceutical formulation comprising treprostinil or its derivative, or a pharmaceutically acceptable salt thereof; and (ii) instructions for use of the metered dose inhaler containing treprostinil in treating pulmonary hypertension.

As used herein, the phrase "instructions for use" shall mean any FDA-mandated labeling, instructions, or package inserts that relate to the administration of Treprostinil or its derivatives, or pharmaceutically acceptable salts thereof, for treatment of pulmonary hypertension by inhalation. For example, instructions for use may include, but are not limited to, indications for pulmonary hypertension, identification of specific symptoms associated with pulmonary hypertension, that can be ameliorated by Treprostinil, recommended dosage amounts for subjects suffering from pulmonary hypertension and instructions on coordination of individual's breathing and actuation of the metered dose inhaler.

The present invention can be illustrated in more detail by the following example, however, it should be understood that the present invention is not limited thereto.

EXAMPLE 1

Open Label Study Upon Acute Safety, Tolerability and Hemodynamic Effects of Inhaled Treprostinil Delivered in Seconds A study was conducted of acute vasodilator challenge during right heart catheter investigation to determine the safety, tolerability and pulmonary vasodilatory potency of inhaled treprostinil applied in seconds by a soft mist inhaler (SMI-TRE). The study produced evidence for a long lasting favourable effect of SMI-TRE on pulmonary hemodynamics in absence of systemic side effects and gas exchange disruptions.

Summary:

Inhaled nitric oxide (20 ppm; n=45) and inhaled treprostinil sodium (TRE; n=41) or placebo (n=4) were applied once during right heart catheter investigation. TRE was delivered in 2 breaths (1000 μg/ml aerosol concentration; 30 μg dose; n=12), 3 breaths (1000 μg/ml; 45 μg; n=9) or 2 breaths (2000 μg/ml; 60 μg; n=20) from a Respimat® SMI. Pulmonary hemodynamics and blood gases were measured at defined time points, observation time following TRE application was 120 minutes. TRE doses of 30 μg, 45 μg and 60 μg reduced pulmonary vascular resistance (PVR) to 84.4±8.7%, 71.4±17.5% and 77.5±7.2% of baseline values, respectively (mean±95% confidence interval). The 120 minute area under the curve for PVR for placebo, 30 µg, 45 µg and 60 µg TRE was 1230±1310, −870±940, −2450±2070 and −2000±900 min %, respectively. Reduction of PVR by a single inhalation of the two higher doses outlasted the observation period of 120 minutes. Reduction of systemic vascular resistance and pressure was negligible, showing a high pulmonary selectivity for SMI-TRE. Intrapulmonary selectivity was also provided by SMI-TRE as ventilation/perfusion matching, assessed by the multiple inert gas elimination technique in 5 patients with gas exchange problems, was not significantly different after SMI-TRE compared to inhaled nitric oxide or no treatment. No significant side effects were observed.

Conclusions: The acute application of inhaled treprostinil with a metered dose inhaler in 2-3 breaths was safe, well tolerated and induced a strong and sustained pulmonary selective vasodilation.

Methods and Patients

A total number of 45 patients with moderate to severe precapillary pulmonary hypertension were enrolled. Patient characteristics were: female to male ratio (f/m)=29/16, age 59±2.3 years, pulmonary artery pressure (PAP) 45±1.8 mmHg, pulmonary vascular resistance (PVR) 743±52 dynes·s·cm$^{-5}$, pulmonary artery wedge pressure (PAWP) 8.6±0.5 mmHg, central venous pressure (CVP) 6.4±0.7 mmHg, cardiac output (CO) 4.5±0.2 l/min, central venous oxygen saturation (SvO2) 62.3±1.2 mmHg (mean±Standard Error of the Mean). Disease etiologies were idiopathic PAH (iPAH) (n=13), PAH other (n=11), chronic thromboembolic pulmonary hypertension (CTEPH) (n=17) and pulmonary fibrosis (n=4). Table 1 presents the patient characteristics of the different groups.

TABLE 1

Patient characteristics of the different treatment groups.

|  | Placebo (n = 4) | 30 µg TRE (n = 12) | 45 µg TRE (n = 9) | 60 µg TRE (n = 20) |
|---|---|---|---|---|
| Age [years] | 61 ± 8 | 53.9 ± 3.9 | 54.2 ± 5.7 | 65.5 ± 3.1 |
| PAP [mmHg] | 49.5 ± 10.1 | 45 ± 3.1 | 54.3 ± 2.8 | 39.7 ± 2.0 |
| PVR [Dynes] | 896 ± 163 | 597 ± 53.9 | 1049 ± 107 | 663 ± 81 |
| CO [l/min] | 4.46 ± 0.9 | 5.2 ± 0.4 | 3.9 ± 0.4 | 4.4 ± 0.3 |
| SAP [mmHg] | 98 ± 8.1 | 90.1 ± 3.2 | 82.8 ± 3.9 | 86.1 ± 2.0 |
| SaO2 [%] | 85.3 ± 4.5 | 90.0 ± 1.1 | 89.6 ± 1.1 | 90.6 ± 0.5 |
| SvO2 [%] | 57.5 ± 3.9 | 66.0 ± 1.6 | 59.1 ± 3.4 | 62.5 ± 1.6 |

Data are given as mean ± Standard Error of the Mean (SEM).
PAP = pulmonary artery pressure;
PVR = pulmonary vascular resistance;
CO = cardiac output;
SAP = systemic arterial pressure;
SaO2 = arterial oxygen saturation;
SvO2 = central venous oxygen saturation.

Baseline values were determined 20-30 minutes after placement of the catheter. Heart rate, pulmonary and systemic blood pressure and cardiac output were measured and blood gases were taken during each pharmacological intervention at defined time points. Pharmacological interventions included the inhalation of 20 ppm nitric oxide (NO) after evaluation of baseline parameters (n=45) and the consecutive inhalation of placebo (n=4), 30 µg SMI-TRE (n=12), 45 µg SMI-TRE (n=9) or 60 µg (n=20) SMI-TRE. Placebo and treprostinil was applied with the Respimat® SMI. For filling of this device with treprostinil sodium, the placebo solution was withdrawn from the device with a syringe and treprostinil solution was injected into the device under sterile conditions. Aerosol quality was controlled before and after refilling of the SMI devices by laser diffractometry, see e.g. Gessler T., Schmehl T., Hoeper M. M., Rose F., Ghofrani H. A., Olschewski H. et al. Ultrasonic versus jet nebulization of iloprost in severe pulmonary hypertension. Eur. Respir. J. 2001; 17:14-19 incorporated herein in its entirety. The aerosol sizes before (placebo) and after filling (treprostinil) were unchanged. The aerosol particles mass median aerodynamic diameter of treprostinil-aerosol was 4-5 µm, which can be at the upper limit for alveolar deposition. The aerosol volume delivered by one cycle from the SMI was 15 µl. The solution used for aerosol generation was prepared from treprostinil sodium salt using a standard protocol. The SMI was either filled with a concentration of 1000 µg/ml treprostinil sodium (one aerosol puff=15 µg TRE) or with 2000 µg/ml (one puff=30 µg TRE). The different doses were applied as 2 puffs 1000 µg/ml (30 µg), 3 puffs 1000 µg/ml (45 µg) and 2 puffs 2000 µg/ml (60 µg). The placebo was inhaled as 2 puffs from a placebo-SMI. Hemodynamics and gas-exchange parameters were recorded for 120 minutes after TRE inhalation. This study used the Respimat® device, because the implemented "soft mist" technology was well suited for the deposition of such highly active drugs like prostanoids.

The impact of SMI-TRE on ventilation-perfusion matching was assessed in five patients (30 µg TRE, n=2; 45 µg TRE, n=1; 60 µg TRE, n=2) with pre-existing gas exchange problems by use of the multiple inert gas elimination technique (MIGET), see e.g. Wagner P D, Saltzman H A, West J B. Measurement of continuous distributions of ventilation-perfusion ratios: theory. J Appl Physiol. 1974; 36:588-99; Ghofrani H A, Wiedemann R, Rose F, Schermuly R T, Olschewski H, Weissmann N et al. Sildenafil for treatment of lung fibrosis and pulmonary hypertension: a randomised controlled trial. Lancet. 2002; 360:895-900, both incorporated herein in their entirety.

Statistics:

Mean values, standard deviation, standard error of the mean and 95% confidence intervals were calculated. Statistical analysis was done by use of a paired t-test.

Results:

The inhalation of treprostinil sodium from the metered dose inhaler (SMI-TRE) was well tolerated, only mild and transient cough for a maximum of one minute was reported. No systemic side effects like headache, flush, nausea or dizziness were observed.

Figure 2:
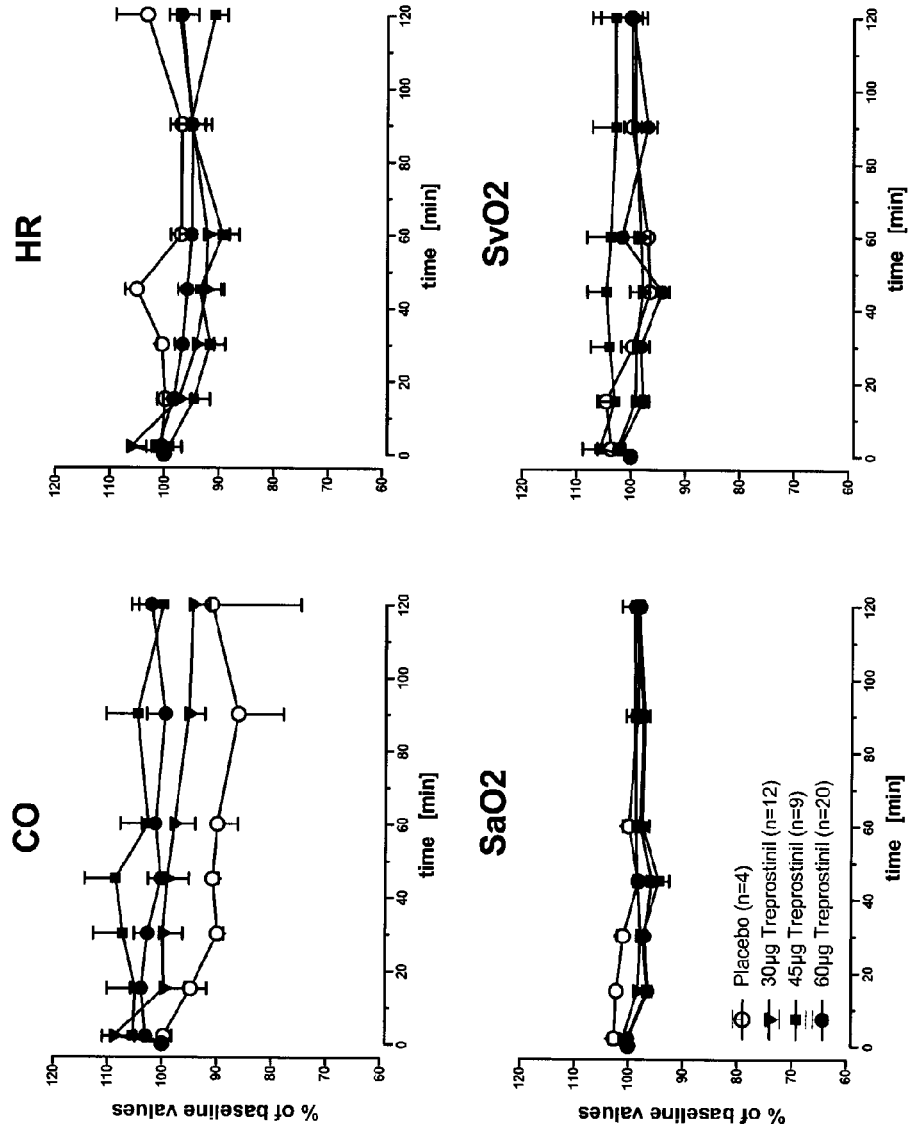
FIG. 2 presents hemodynamic changes induced by the inhalation of placebo (open circles), 30 µg treprostinil (triangles), 45 µg treprostinil (squares) or 60 µg treprostinil (black circles) applied by a metered dose inhaler. Treprostinil induced sustained elevation of cardiac output. Heart rate was rather unchanged as a sign for low spillover of MDI-TRE to the systemic circulation. Gas exchange was not negatively affected. CO=cardiac output; HR=heart rate; SaO2=arterial oxygen saturation; SvO2=central venous oxygen saturation. Data are given as mean value±SEM.

Two to three breaths of SMI-TRE induced a strong pulmonary vasodilation that outlasted the observation time of 120 minutes (45 and 60 µg). The lower dose of 30 µg TRE induced a somewhat shorter effect on pulmonary vascular resistance; however, the maximal pulmonary vasodilation was comparable. In contrast, placebo inhalation did not induce pulmonary vasodilation. In fact a slight increase in PVR over the time of the right heart catheter investigation could be recorded following placebo inhalation (FIG. 1). The effect of SMI-TRE on systemic vascular resistance and pressure was very small and not clinically significant. Cardiac output was significantly increased over the whole observation period, whereas heart rate was rather unchanged. Gas exchange was not influenced by SMI-TRE (FIG. 2). The maximal changes in hemodynamic and gas-exchange parameters compared to baseline values are depicted in Table 2.

TABLE 2

Extremes of the relative changes of hemodynamic and gas exchange parameters compared to baseline after inhalation of Placebo (n = 4), 30 μg treprostinil (n = 12), 45 μg treprostinil (n = 9) and 60 μg treprostinil (n = 20). Highest (max) and lowest (min) values during the observation period are shown.

|  | Placebo | 30 μg TRE | 45 μg TRE | 60 μg TRE |
|---|---|---|---|---|
| PAP (min) | 99.4 ± 3.0 | 83.4 ± 3.2 | 77.6 ± 6.8 | 79.5 ± 2.4 |
| PVR (min) | 101.4 ± 1.9 | 84.4 ± 4.4 | 71.4 ± 8.9 | 77.5 ± 3.7 |
| CO (max) | 99.7 ± 1.1 | 108.8 ± 3.8 | 108.6 ± 5.6 | 103.8 ± 2.0 |
| SVR (min) | 104.3 ± 4.3 | 97.7 ± 4.2 | 92 ± 3.9 | 91.3 ± 2.1 |
| SAP (min) | 102.7 ± 1.7 | 97.3 ± 1.9 | 96.1 ± 1.5 | 93.6 ± 2.9 |
| HR (max) | 105 ± 2.1 | 106.1 ± 2.9 | 99.1 ± 2.4 | 101.1 ± 0.9 |
| SaO2 (min) | 98.2 ± 0.4 | 101 ± 0.3 | 94.4 ± 1.8 | 95.8 ± 0.9 |
| SvO2 (max) | 104.5 ± 1.4 | 102.4 ± 1.3 | 104.5 ± 4.4 | 102 ± 1.0 |

Data are given as percent of baseline values (mean ± SEM).
PAP = pulmonary artery pressure;
PVR = pulmonary vascular resistance;
SVR = systemic vascular resistance;
CO = cardiac output;
SAP = systemic arterial pressure;
HR = heart rate;
SaO2 = arterial oxygen saturation;
SvO2 = central venous oxygen saturation.

Figure 3:
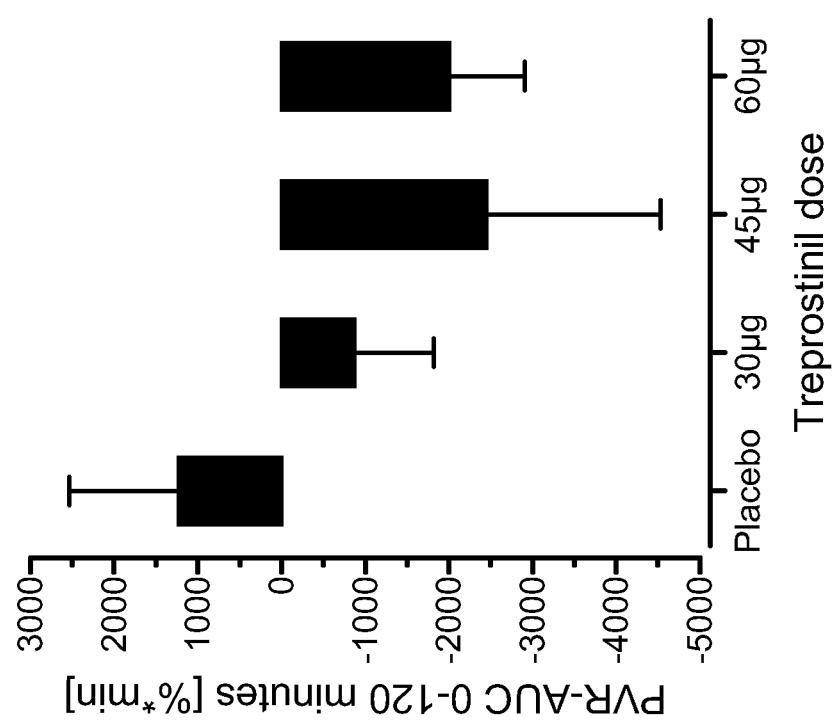
FIG. 3 shows areas under the curve for changes in pulmonary vascular resistance (PVR) calculated for an observation period of 120 minutes after inhalation treprostinil using a metered dose inhaler. PVR was markedly lowered by treprostinil inhalation. The increased pulmonary vasodilation over time with the two highest doses mainly relies on the more sustained effect over time. Data are shown as mean value±95% confidence intervals.

The areas under the curve for PVR were calculated for placebo and the different SMI-TRE doses over the 120 minute observation period (FIG. 3). A dose effect of SMI-TRE with a trend to a more sustained effect with the two highest doses could be observed.

Figure 4:
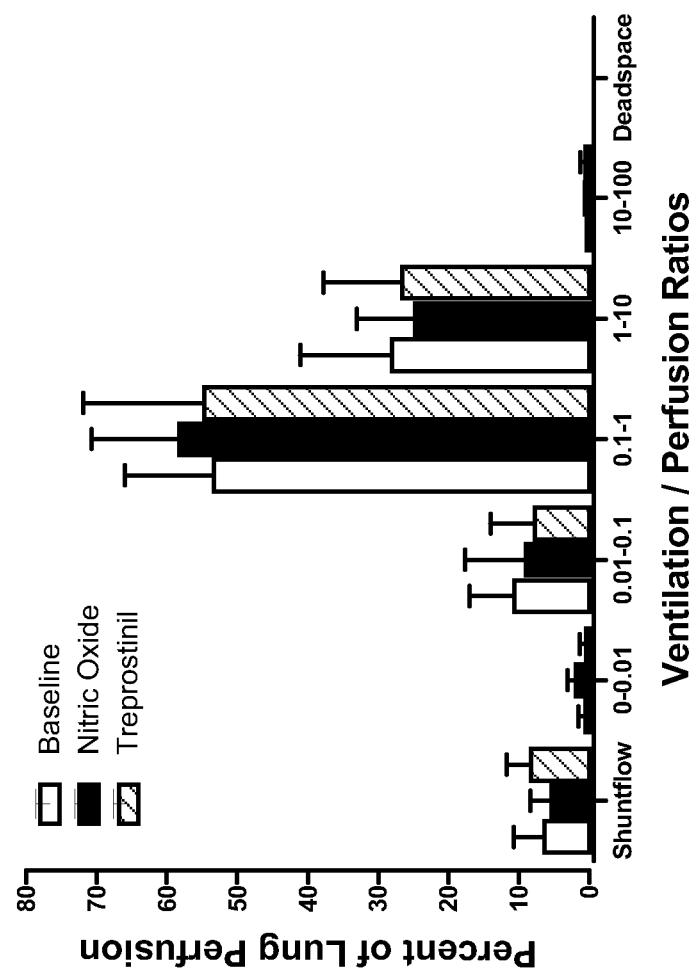
FIG. 4 demonstrates Ventilation-perfusion matching measured with the multiple inert gas elimination technique. Five patients (30 µg TRE, n=2; 45 µg TRE, n=1; 60 µg TRE, n=2) with pre-existing gas exchange problems were investigated for changes in ventilation-perfusion ratios. All patients had significant shunt flow at baseline. Shunt-flow and low V/Q areas were not significantly changed by nitric oxide (NO) inhalation or treprostinil inhalation using a metered dose inhaler (MDI-TRE). MDI-TRE applied at high treprostinil concentrations did not negatively affect ventilation-perfusion matching and gas-exchange. Data are given as mean value±95% confidence intervals.

The inhalation of a highly concentrated aerosol can be in theory prone to disturbances of gas exchange because the deposition of even small amounts of aerosol may deliver high doses locally and thereby antagonize the hypoxic pulmonary vasoconstriction in poorly ventilated areas. This would then lead to increased shunt flow or increase of low ventilation/perfusion (V/Q) areas. This question was addressed in five patients with the multiple inert gas elimination technique (MIGET), the gold-standard for intrapulmonary V/Q ratio determination. The MIGET patients were selected for pre-existing gas exchange limitations. Characteristics of these patients were: PAP 54.6±3.2 mmHg, PVR 892±88 dynes, SaO2 91.7±0.5%, SvO2 65.2±1.8%. Etiologies were iPAH (n=1), CTEPH (n=3), pulmonary fibrosis (n=1). The maximal relative reduction of SaO2 after inhalation of SMI-TRE in these patients was −3.8±1.5% compared to baseline values. Shunt flow at baseline, NO-inhalation and 60 minutes after SMI-TRE was 6.4±4.3%, 5.4±3.0% and 8.3±3.4%, respectively (mean±95% confidence interval; FIG. 4).

No significant increase in low V/Q areas or shunt fraction after inhalation of SMI-TRE was observed, in fact the distribution of perfusion was not different to that at baseline and during nitric oxide inhalation. This proves an excellent intra-pulmonary selectivity of SMI-TRE, which is also reflected by unchanged arterial oxygen saturation.

Conclusion:

Treprostinil is tolerated at high doses with no systemic side effects. The application of an effective amount of treprostinil in only few or even one single breath was achieved with a highly concentrated treprostinil sodium solution. Treprostinil can be applied by a metered dose inhaler, such as Respimat® soft mist inhaler.

EXAMPLE 2

Investigation of the Effects of Inhaled Treprostinil on Pulmonary Hemodynamics and Gas Exchange in Severe Pulmonary Hypertension This study investigated the effects of inhaled treprostinil on pulmonary vascular resistance in severe pulmonary hypertension and addressed systemic effects and gas exchange as well as tolerability and efficacy of high doses of treprostinil given in short time. A total of 123 patients with a mean pulmonary artery pressure of about 50 mmHg were investigated in three separate randomized studies Inhaled treprostinil exerted potent sustained pulmonary vasodilation with excellent tolerability and could be safely applied in a few breaths or even one breath.

Summary:

Three different studies were conducted on a total of 123 patients by means of right heart catheterization: i) a randomized crossover-design study (44 patients), ii) a dose escalation study (31 patients) and iii) a study of reduction of inhalation time while keeping the dose fixed (48 patients). The primary endpoint was the change in pulmonary vascular resistance (PVR).

The mean pulmonary artery pressure of the enrolled patients was about 50 mmHg. Hemodynamics and patient characteristics were similar in all studies. In study i) TRE and Iloprost (ILO), at an inhaled dose of 7.5 μg, displayed comparable PVR decrease, with a significantly different time course (p<0.001), TRE exhibiting a more sustained effect on PVR (p<0.0001) and less systemic side effects. In study ii) placebo, 30 μg, 60 μg, 90 μg or 120 μg TRE were applied with drug effects being observed for 3 hours after inhalation. A near-maximal acute PVR decrease was observed at 30 μg TRE. In study iii) TRE was inhaled with a pulsed ultrasonic nebulizer, mimicking a metered dose inhaler. 15 μg TRE was inhaled with 18 pulses (TRE concentration 100 μg/ml), 9 pulses (200 μg/ml), 3 pulses (600 μg/ml), 2 pulses (1000 μg/ml) or 1 pulse (2000 μg/ml), each mode achieving comparable, sustained pulmonary vasodilation.

Inhaled treprostinil exerts sustained pulmonary vasodilation with excellent tolerability at doses, which may be inhaled in a few or even one breath Inhaled treprostinil is advantageous to inhaled iloprost in terms of duration of effect and systemic side effects Inhaled treprostinil is well tolerated in concentrations up to 2000 mg/ml (bringing down inhalation time to a single breath) and in high doses (up to 90 μg).

Methods:

All inhalations were performed with the OPTINEB® ultrasonic nebulizer (Nebutec, Elsenfeld, Germany).

Study i) was a randomized, open-label, single-blind crossover study. The primary objective was to compare the acute hemodynamic effects and the systemic side effects of inhaled treprostinil with inhaled iloprost at comparable doses. A total number of 44 patients with moderate to severe precapillary pulmonary hypertension were enrolled. Patient characteristics and hemodynamic as well as gas exchange parameters are outlined in Table 3.

TABLE 3

Patient characteristics, hemodynamic parameters and gas exchange values at baseline, before challenge with inhalative prostanoids.

| | N | Age | Gender f/m | Etiology i/o/t/f | PAP [mmHg] | PVR [dyn*s*cm⁻⁵] | SAP [mmHg] | CVP [mmHg] | PAWP [mmHg] | CO [l/min] | SaO2 [%] | SvO2 [%] |
|---|---|---|---|---|---|---|---|---|---|---|---|---|
| 1a | 14 | 55.1 ± 4.8 | 11/3 | 4/4/2/4 | 53.8 ± 3.1 | 911 ± 102 | 95.4 ± 3.6 | 7.4 ± 1 | 8.0 ± 0.8 | 4.3 ± 0.4 | 93.8 ± 2 | 63.9 ± 2.4 |
| 1b | 14 | 54.1 ± 3.3 | 10/4 | 1/6/5/2 | 47.4 ± 3.8 | 716 ± 80 | 90.6 ± 3.3 | 5.9 ± 1.4 | 6.4 ± 0.7 | 4.7 ± 0.4 | 92 ± 1 | 64.4 ± 2.3 |
| 1c | 16 | 56 ± 2.9 | 7/9 | 6/3/6/1 | 47.5 ± 4.5 | 777 ± 102 | 92 ± 4.5 | 8.3 ± 1.4 | 8.6 ± 1.4 | 4.4 ± 0.5 | 91.4 ± 0.9 | 59.8 ± 2.6 |
| 2a | 8 | 60.8 ± 4 | 4/4 | 2/2/3/1 | 51.9 ± 4.9 | 849 ± 152 | 95.9 ± 4.8 | 7.6 ± 1.4 | 11.1 ± 1.7 | 4.4 ± 0.6 | 89.6 ± 2.8 | 60.1 ± 2.8 |
| 2b | 8 | 52.8 ± 6.6 | 6/2 | 1/3/3/1 | 49 ± 4 | 902 ± 189 | 92.4 ± 2.4 | 4.8 ± 1.1 | 7.2 ± 1.3 | 4.0 ± 0.4 | 92.4 ± 2.4 | 62.5 ± 1.7 |
| 2c | 6 | 56.8 ± 5.9 | 4/2 | 0/2/2/2 | 44.2 ± 3.5 | 856 ± 123 | 96.3 ± 3.9 | 5 ± 1.1 | 6 ± 1 | 3.8 ± 0.3 | 92.8 ± 1.5 | 63.6 ± 1.8 |
| 2d | 6 | 51.2 ± 3.8 | 4/2 | 2/2/2/0 | 55.5 ± 4.9 | 940 ± 110 | 91.2 ± 8.1 | 11.2 ± 1.2 | 10 ± 0.7 | 3.9 ± 0.4 | 92 ± 1.9 | 62 ± 5.8 |
| 2e | 3 | 57.3 ± 9.1 | 1/2 | 0/1/0/2 | 45.3 ± 5.2 | 769 ± 267 | 99 ± 3.2 | 5 ± 2.1 | 9 ± 0.6 | 4.5 ± 0.6 | 94.2 ± 1.3 | 66.3 ± 1.5 |
| 3a | 6 | 52.7 ± 6.6 | 4/2 | 2/4/0/0 | 53.8 ± 6.7 | 928 ± 145 | 92.7 ± 7.9 | 8.7 ± 2.7 | 8.8 ± 1.3 | 4.2 ± 0.6 | 90.4 ± 2.8 | 64.8 ± 4.3 |
| 3b | 6 | 58.3 ± 3.5 | 4/2 | 3/1/1/1 | 54.2 ± 6.1 | 808 ± 156 | 94.3 ± 2.8 | 7 ± 1.4 | 10 ± 1.3 | 5 ± 0.7 | 91.9 ± 0.7 | 63.5 ± 2.9 |
| 3c | 21 | 57.4 ± 5.6 | 8/3 | 7/7/6/1 | 46.1 ± 2.5 | 900 ± 99 | 88 ± 2.8 | 9 ± 1.4 | 9.2 ± 0.5 | 3.7 ± 0.3 | 91.7 ± 0.5 | 59.7 ± 2 |
| 3d | 7 | 55.6 ± 5.8 | 3/4 | 0/4/3/0 | 53.1 ± 7.1 | 732 ± 123 | 91.4 ± 5.6 | 7.9 ± 3.1 | 8.6 ± 1.3 | 5 ± 0.4 | 90.7 ± 1.4 | 61.3 ± 3.7 |
| 3e | 8 | 59 ± 5.2 | 7/1 | 0/4/4/0 | 45.1 ± 3.9 | 733 ± 114 | 92.8 ± 6.8 | 4.6 ± 0.8 | 8.1 ± 1.1 | 4.3 ± 0.2 | 90.7 ± 0.8 | 66.3 ± 2.8 |

Group 1 corresponds to study i); randomized crossover study comparing inhaled iloprost (ILO) and inhaled treprostinil (TRE).
a = 7.5 g ILO vs. 7.5 μg TRE,
b = 7.5 g ILO vs. 15 μg TRE (6 min inhalation time),
c = 7.5 g ILO vs. 15 μg TRE (3 min inhalation time).
Group 2 corresponds to study ii); evaluation of maximal tolerated dose of TRE.
a = placebo inhalation,
b = 30 μg TRE,
c = 60 μg TRE,
d = 90 μg TRE,
e = 120 μg TRE.
Group 3 corresponds to study iii); reduction of inhalation time by increase of TRE concentration, aiming at a total inhaled dose of 15 μg.
a = 18 pulses of 100 μg/ml TRE,
b = 9 pulses of 200 μg/ml TRE,
c = 3 pulses of 600 μg/ml TRE,
d = 2 pulses of 1000 μg/ml TRE,
e = 1 pulse 2000 μg/ml TRE.
Etiology of pulmonary hypertension was classified as idiopathic PAH (i), PAH of other causes (o), chronic thromboembolic PH (t), and pulmonary fibrosis (f).

Each patient inhaled both iloprost and treprostinil on the same day during right heart catheter investigation; the drugs were administered consecutively with a one hour interval between the drug applications. One half of the study patients initially inhaled treprostinil and then inhaled iloprost (n=22), while the other half initially inhaled iloprost and then inhaled treprostinil (n=22). Patients were randomized to one of the two groups and blinded as to the study drugs. Drug effects were monitored for 60 minutes after each inhalation. Iloprost was inhaled at 4 μg/ml (6 min inhalation time; n=44) and treprostinil was inhaled at a concentration of 4 μg/ml (6 min inhalation; n=14), 8 μg/ml (6 min inhalation; n=14) or 16 μg/ml (3 min inhalation; n=16). Based on previous biophysical characterization of the ultrasonic device with iloprost- and treprostinil-solution, this corresponds to a total inhaled dose of 7.5 μg iloprost and treprostinil (4 μg/ml) and 15 μg treprostinil (8 μg/ml and 16 μg/ml), respectively.

Study ii) was a randomized, open-label, single blind, placebo controlled study. The primary objectives were to describe the pharmacodynamic and pharmacokinetic effects of inhaled treprostinil at a well tolerated dose (30 μg) and to explore the highest tolerated single dose. A total number of 31 patients inhaled either placebo or treprostinil; each patient received one inhalation. The first 16 patients were randomized to 30 μg TRE (16 μg/ml, n=8) or placebo (stock solution in a concentration corresponding to TRE 16 μg/ml). Subsequent patients received 60 μg TRE (32 μg/ml; n=6), 90 μg TRE (48 μg/ml; n=6) and 120 μg TRE (64 μg/ml; n=3). Inhalation time was 6 minutes in all groups. Hemodynamics and gas-exchange as well as arterial treprostinil concentrations were recorded for 180 minutes.

Study iii) was a randomized, open-label, single blind study. The primary objective was to explore the shortest possible inhalation time for a 15 μg dose of inhaled treprostinil. A total of 48 patients inhaled one dose of TRE during right heart catheter investigation. The drug was applied in 18, 9, 3, 2 or 1 breaths. The aerosol was generated by a pulsed ultrasonic nebulizer (OPTINEB® Nebutec, Elsenfeld, Germany) in cycles consisting of 2 seconds aerosol production (pulse) and 4 seconds pause. The device included an opto-acoustical trigger for the patient to synchronize the inspiration to the end of the aerosol pulse, thereby providing exact dosage. The TRE dose of 15 μg was either generated during 18 cycles (OPTINEB® filled with 100 μg/ml TRE, n=6), 9 cycles (200 μg/ml TRE, n=6), 3 cycles (600 μg/ml TRE, n=21), 2 cycles (1000 μg/ml TRE, n=7) or 1 cycle (2000 μg/ml TRE, n=8). Hemodynamics and gas exchange were recorded for 120-180 minutes.

Treprostinil plasma concentrations were assessed in study ii) at 10, 15, 30, 60 and 120 minutes after inhalation. Treprostinil quantification was done by Alta Analytical Laboratory (El Dorado Hills, Calif., USA) with a validated liquid chromatography atmospheric-pressure ionization tandem mass spectrometry as previously described Wade M., et al. J. Clin. Pharmacol. 2004; 44:503-9. Mixed venous blood was drawn at the depicted time points (FIG. 11) after inhalation, centrifuged and the plasma frozen at −80° C. until temperature controlled shipping on dry ice.

Statistics:

For statistical analysis of study i) the repeated PVR measurements after inhaled iloprost and treprostinil were subjected to a three-factorial analysis of variance (ANOVA; factors: time (A), drug (B), treprostinil concentration (C)) to avoid multiple testing. The time to maximum PVR decrease after inhalation of iloprost versus treprostinil was compared by paired t-test. Area under the curve (AUC) was calculated from start of inhalation until 60 min after inhalation. Means, standard error of the mean (SEM) and 95% confidence intervals were calculated. For study ii) and iii) areas between curves (ABC) were calculated between placebo inhalation (study ii) and the respective treprostinil inhalation until 180 min (study ii)) and 120 min (study iii)) after end of inhalation.

Figure 5:
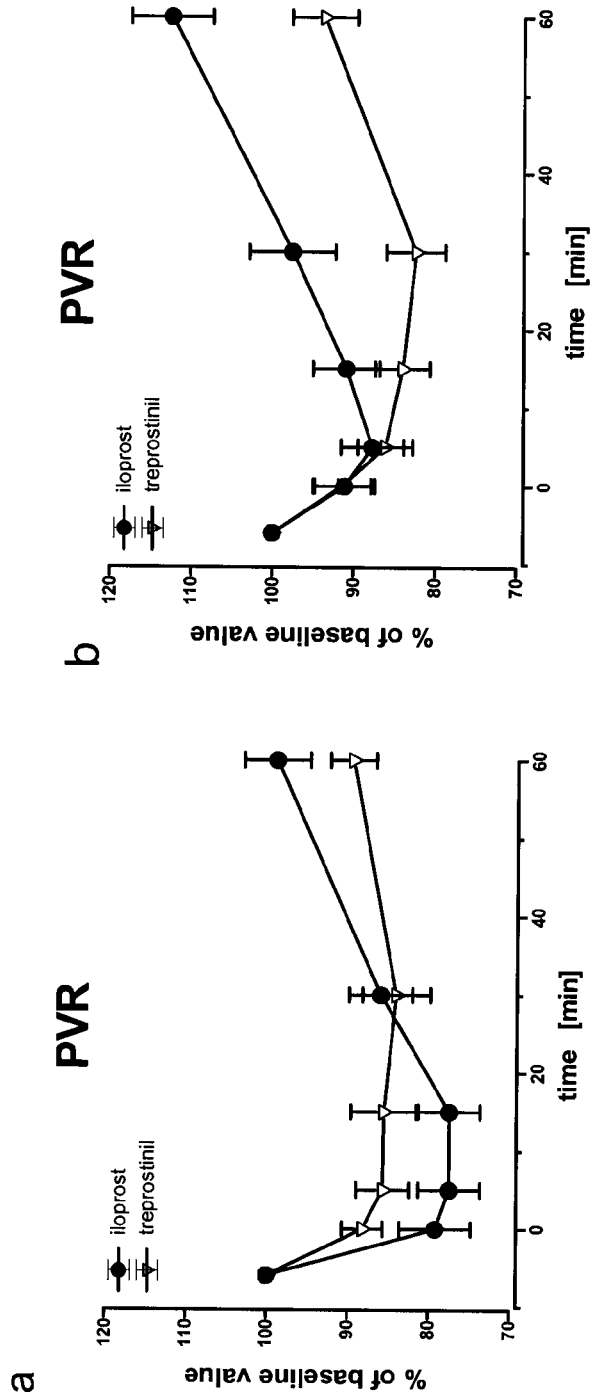
FIG. 5 presents response of pulmonary vascular resistance (PVR) to inhaled treprostinil vs. iloprost—period effects. a) First inhalation with treprostinil (n=22) vs. first inhalation with iloprost (n=22); b) second inhalation with treprostinil (n=22) vs. second inhalation with iloprost (n=22). The PVR decrease with treprostinil was delayed and prolonged, compared to iloprost. Due to carryover effects from the first period, in the second period, the effects of both drugs appeared shortened. Data are shown as percent of baseline values (mean value±95% confidence interval).
Figure 6:
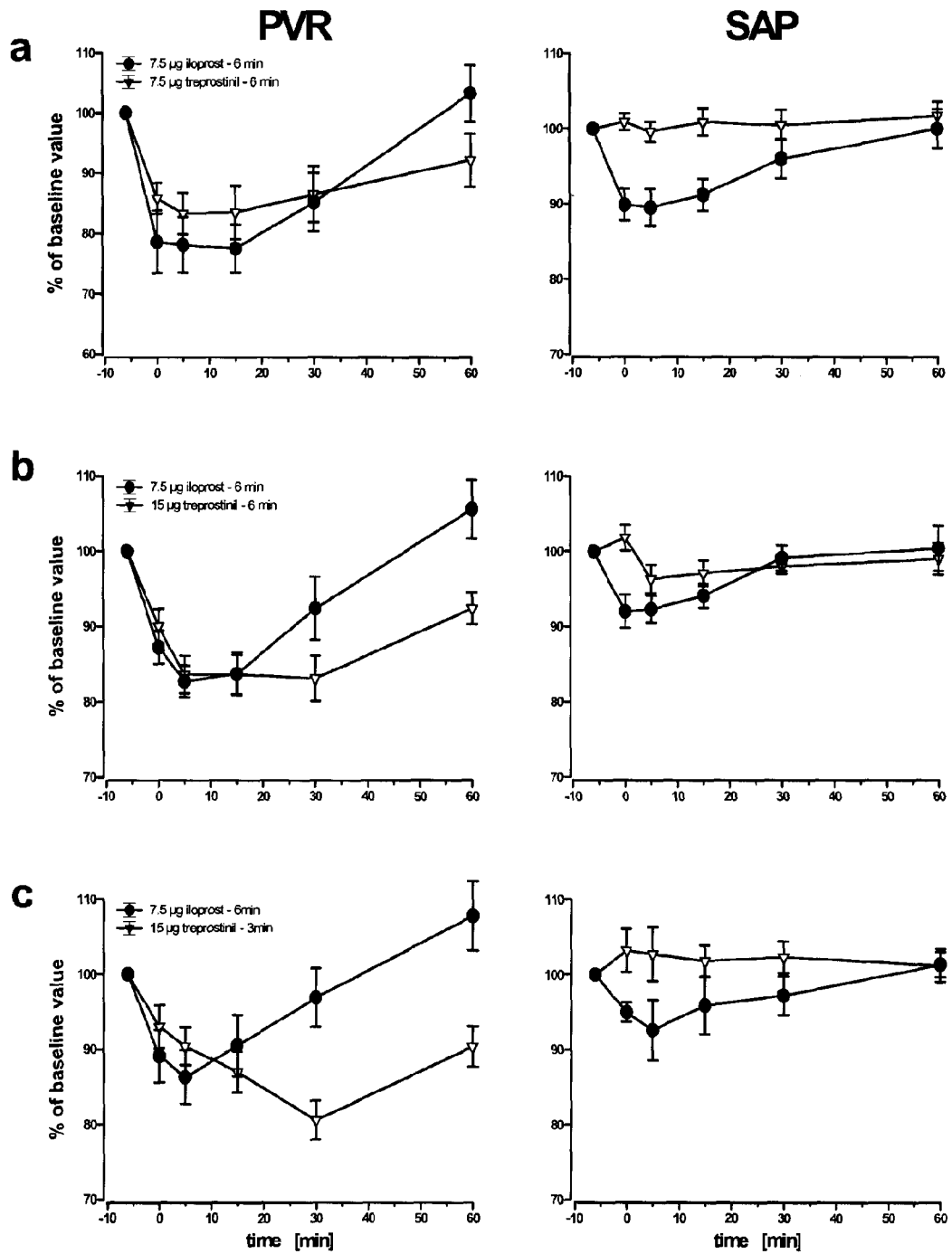
FIG. 6 presents response of PVR and systemic arterial pressure (SAP) to inhalation of treprostinil vs. iloprost—dose effects. a) Inhalation of 7.5 µg iloprost (in 6 min) vs. 7.5 µg treprostinil (6 min) (n=14, in a randomized order). b) Inhalation of 7.5 µg iloprost (6 min) vs. 15 µg treprostinil (6 min) (n=14, in randomized order). c) Inhalation of 7.5 µg iloprost (6 min) vs. 15 µg treprostinil (3 min) (n=16, in randomized order). Data are shown as percent of baseline values (mean±95% confidence interval). Iloprost, filled circles; Treprostinil, open triangles.
Figure 7:
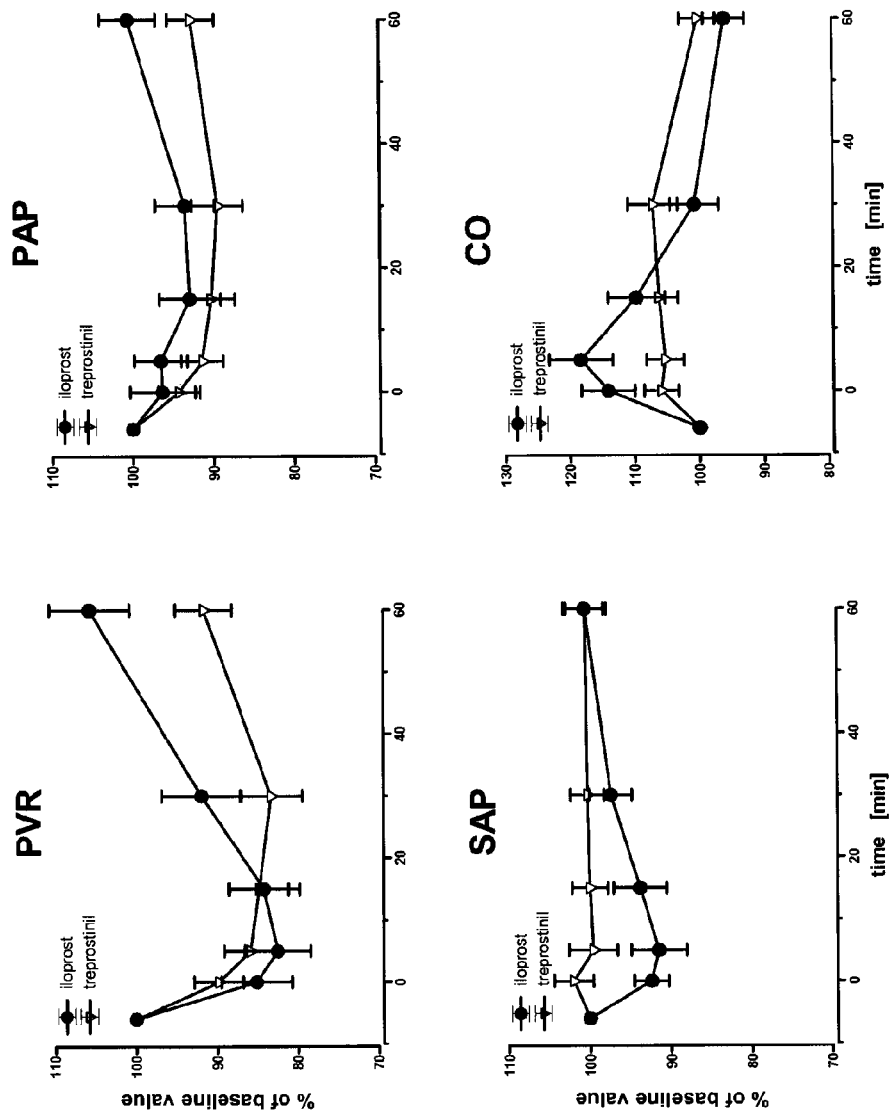
FIG. 7 presents hemodynamic response to inhalation of treprostinil vs. iloprost. Data from n=44 patients, who inhaled both drugs in randomized order, shown as percent of baseline values (mean value±95% confidence interval). PVR, pulmonary vascular resistance; PAP, mean pulmonary arterial pressure; SAP, mean systemic arterial pressure; CO, cardiac output.

Results:

The inhalation of iloprost as well as treprostinil in study i) resulted in a rapid decrease in PVR and PAP (FIG. 5-7). No significant differences were observed for the areas under the curve (AUC) of PVR decrease after inhalation of 7.5 µg TRE in 6 minutes (AUC −12.6±7.0%), 15 µg TRE in 6 minutes (AUC −13.3±3.2%) and 15 µg TRE in 3 minutes (AUC −13.6±4.3%). The AUC for PVR after the inhalation of 7.5 µg iloprost in 6 minutes was −7.7±3.7% (mean±95% confidence interval). An overview of the pooled data of treprostinil inhalation as compared to iloprost inhalation is given in FIG. 7. The maximum effect of iloprost and treprostinil on PVR was comparable but this effect was reached significantly later after treprostinil inhalation (18±2 min) compared to iloprost (8±1 min; mean±SEM, p<0.0001) and lasted considerably longer (after 60 min, PVR values in the treprostinil group had not yet returned to baseline). The increase in cardiac output was less acute but prolonged after treprostinil inhalation. Systemic arterial pressure (SAP) was unaffected by treprostinil inhalation, whereas a transient decrease was observed after iloprost inhalation. Iloprost and treprostinil did not affect gas exchange. Three-factorial ANOVA for PVR demonstrated a significant difference between repeated measurements after inhalation ($p_{(A)}$<0.0001), no significant difference between drugs ($p_B$=0.1), no difference between treprostinil concentrations ($p_{(C)}$=0.74) and a significant drug×time interaction ($p_{(A×B)}$<0.0001). This translates into a significant effect of both drugs on PVR with comparable drug potency but a prolonged drug effect of treprostinil compared to iloprost.

In this study the occasionally observed mild side effects of iloprost inhalation at the given dose (transient flush, headache) were not observed with inhaled treprostinil. Bad taste was reported by most of the patients after inhalation of TRE. This was later found to be attributable to the metacresol preservative contained in the treprostinil solution.

Figure 8:
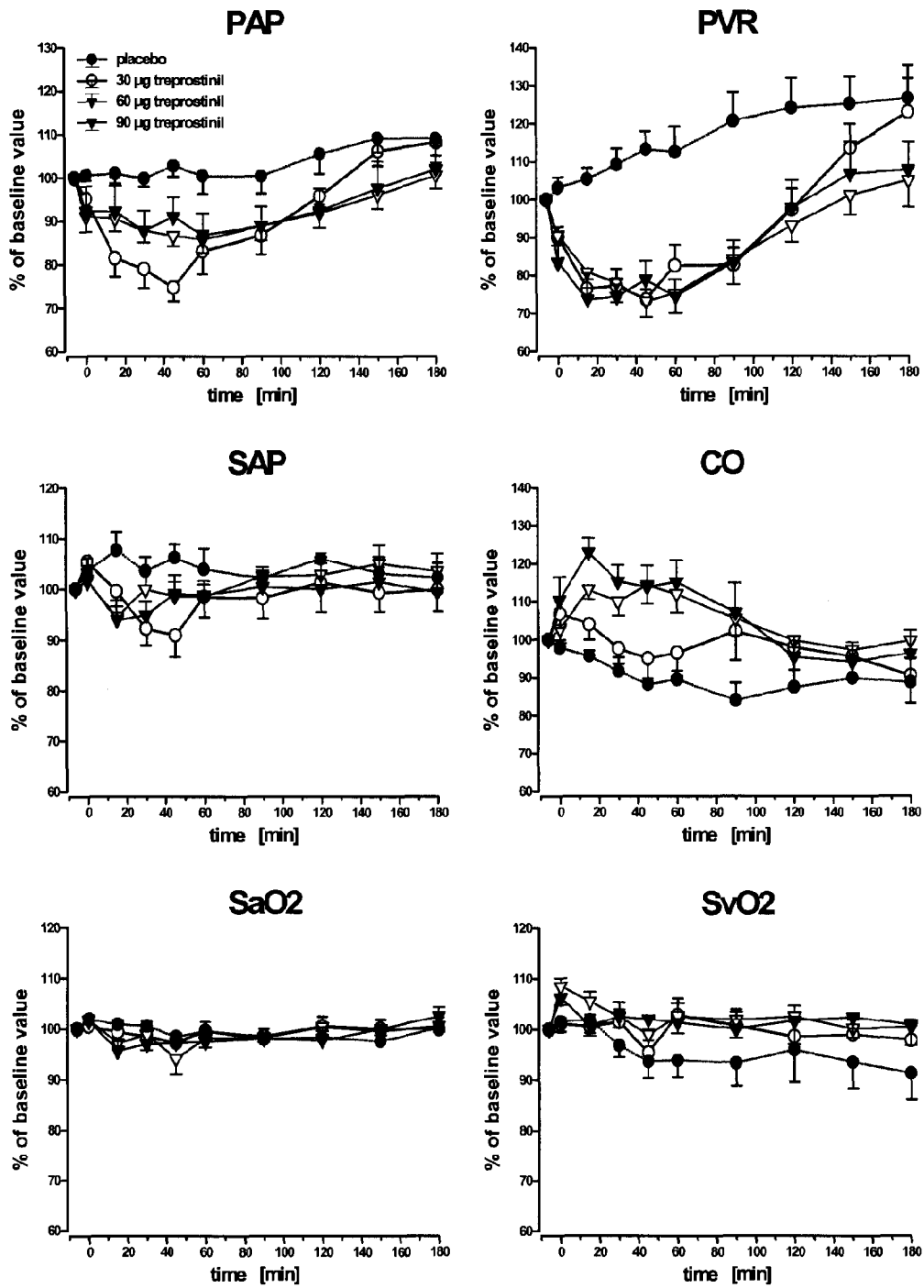
FIG. 8 presents pharmacodynamics after treprostinil inhalation vs. placebo. Placebo or treprostinil in doses of 30 µg, 60 µg or 90 µg were inhaled (means±95% confidence intervals). Maximal decrease of PVR was comparable for all doses. The duration of pulmonary vasodilation (PVR-decrease) appeared to be dose dependent. PVR, pulmonary vascular resistance; PAP, mean pulmonary arterial pressure; SAP, mean systemic arterial pressure; CO, cardiac output; SaO2, arterial oxygen saturation; SvO2, mixed venous oxygen saturation.
Figure 9:
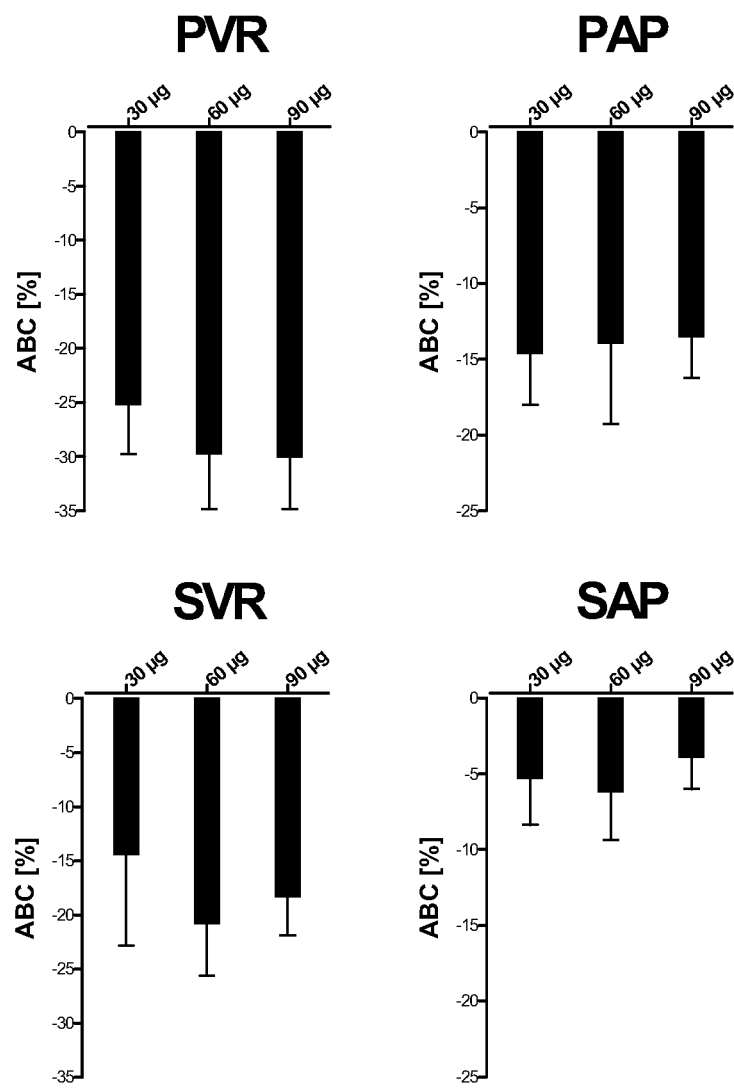
FIG. 9 presents Areas Between the placebo and the treprostinil Curves (ABC). ABCs were calculated for a 3-hour period after inhalation of TRE or placebo from the relative changes of hemodynamic parameters (means±95% confidence intervals). PVR, pulmonary vascular resistance; PAP, mean pulmonary arterial pressure; SAP, mean systemic arterial pressure; SVR, systemic vascular resistance.

In study ii) pharmacodynamics of inhaled placebo or treprostinil were observed for 180 minutes. Placebo inhalation was followed by a gradual increase in PVR over the entire observation time. Due to reduced patient numbers in the 120 µg TRE group (because of side effects, see below), the hemodynamic values for this group were not included in the graphs of this study (FIG. 8-9). All TRE doses lead to comparable maximal decreases of PVR to 76.5±4.7% (30 µg), 73.7±5.8% (60 µg), 73.3±4.3% (90 µg) and 65.4±4.1% (120 µg) of baseline values. An extended duration of pulmonary vasodilation was noted, surpassing the 3 hour observation period for the 60 µg and 90 µg (and 120 µg) TRE doses, whereas in the 30 µg dose group the hemodynamic changes had just returned to baseline within this period. Even at the highest doses, TRE had only minor effects on systemic arterial pressure (FIG. 8). Cardiac output was increased to a maximum of 106.8±3.2% (30 µg), 122.9±4.3% (60 µg), 114.3±4.8% (90 µg) and 111.3±3.9% (120 µg TRE). The areas between the response curves after placebo versus TRE inhalation were calculated for PVR, PAP, SVR and SAP (FIG. 9). Areas between the curves for PVR were not significantly different for 30 µg, 60 µg and 90 µg TRE, a nearly maximal effect on PVR was already observed with 30 µg TRE. Effects on PAP and SAP were small and did not show a dose-response relationship. Gas exchange was not affected at doses up to 90 µg TRE, but arterial oxygen saturation was significantly decreased at a dose of 120 µg TRE in all 3 patients. Further dose increments were omitted due to this side effect and severe headache in one patient.

Again, bad taste of the TRE aerosol was reported by most patients. Other side effects were flushing (n=1; 30 µg TRE), mild transient cough (n=3; 60 µg TRE), mild transient bronchoconstriction that resolved after one inhalation of fenoterol (n=1; 30 µg TRE), moderate bronchoconstriction that resolved after one inhalation of fenoterol (n=1; 120 µg TRE), and severe headache (n=1; 120 µg TRE). The bad taste, the bronchoconstriction and the drop in SaO2 was attributed to metacresol in the original TRE solution. With the use of a metacresol-free solution of TRE (University Hospital Giessen, Germany; produced according to the manufacturer's protocol) in the following study, these side effects did no longer occur.

Study iii) was performed with metacresol-free TRE solution, having no specific taste and smell. A total of 48 patients were enrolled. This study aimed at the reduction of inhalation time and aerosol volume needed for pulmonary drug delivery. A modified OPTINEB® inhalation device was programmed to produce a constant amount of aerosol during repeatable pulses of aerosol generation. With this device, treprostinil could be safely utilized up to a concentration of 2000 Ξg/ml without considerable side effects. No relationship of number or type of side effects to TRE concentration was observed. Reported side effects were mild transient cough (n=6), mild headache (n=2) and mild jaw pain (n=1).

Figure 10:
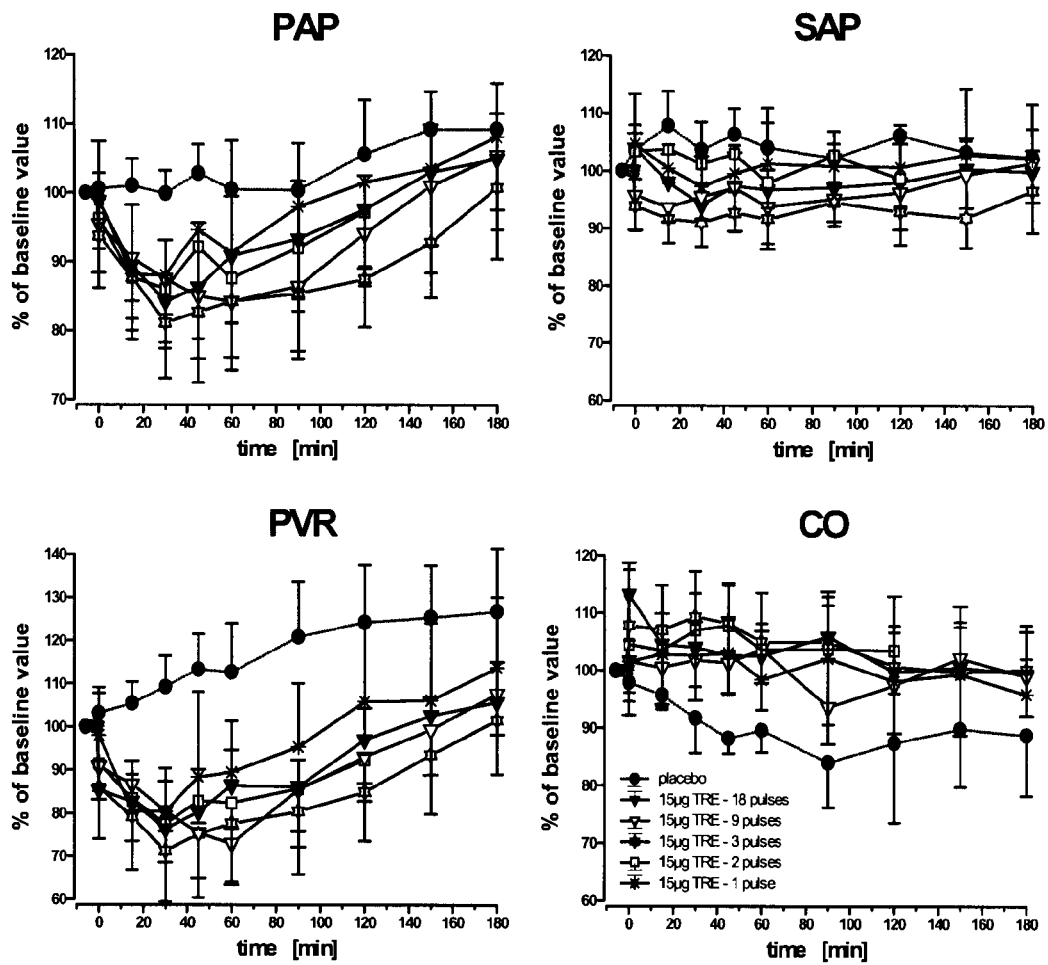
FIG. 10 presents hemodynamic responses to the inhalation of 15 µg treprostinil. The inhalation time by increasing treprostinil concentration. A pulse of aerosol was generated every 6 seconds. TRE aerosol was inhaled in concentrations of 100 µg/ml (18 pulses; n=6), 200 µg/ml (9 pulses; n=6), 600 µg/ml (3 pulses; n=21), 1000 µg/ml (2 pulses; n=7) and 2000 µg/ml (1 pulse; n=8). Placebo data correspond to FIG. 8. Data are shown as means±95% confidence intervals. PVR, pulmonary vascular resistance; PAP, mean pulmonary arterial pressure; SAP, mean systemic arterial pressure; CO, cardiac output.

The reduction of PVR and PAP was comparable between all groups (FIG. 10). TRE inhalation reduced PVR to 76.3±5.6% (18 pulses, 100 µg/ml), 72.9±4.9% (9 pulses, 200 µg/ml), 71.2±6.0% (3 pulses, 600 µg/ml), 77.4±4.5% (2 pulses, 1000 µg/ml) and 80.3±5.2% (1 pulse, 2000 µg/ml). PAP was reduced to 84.2±4.5% (18 pulses, 100 µg/ml), 84.2±4.1% (9 pulses, 200 µg/ml), 81.1±4.1% (3 pulses, 600 µg/ml), 86±4% (2 pulses, 1000 µg/ml) and 88±5.4% (1 pulse, 2000 µg/ml). Cardiac output was moderately increased in all groups, whereas systemic arterial pressure was not significantly affected.

Figure 11:
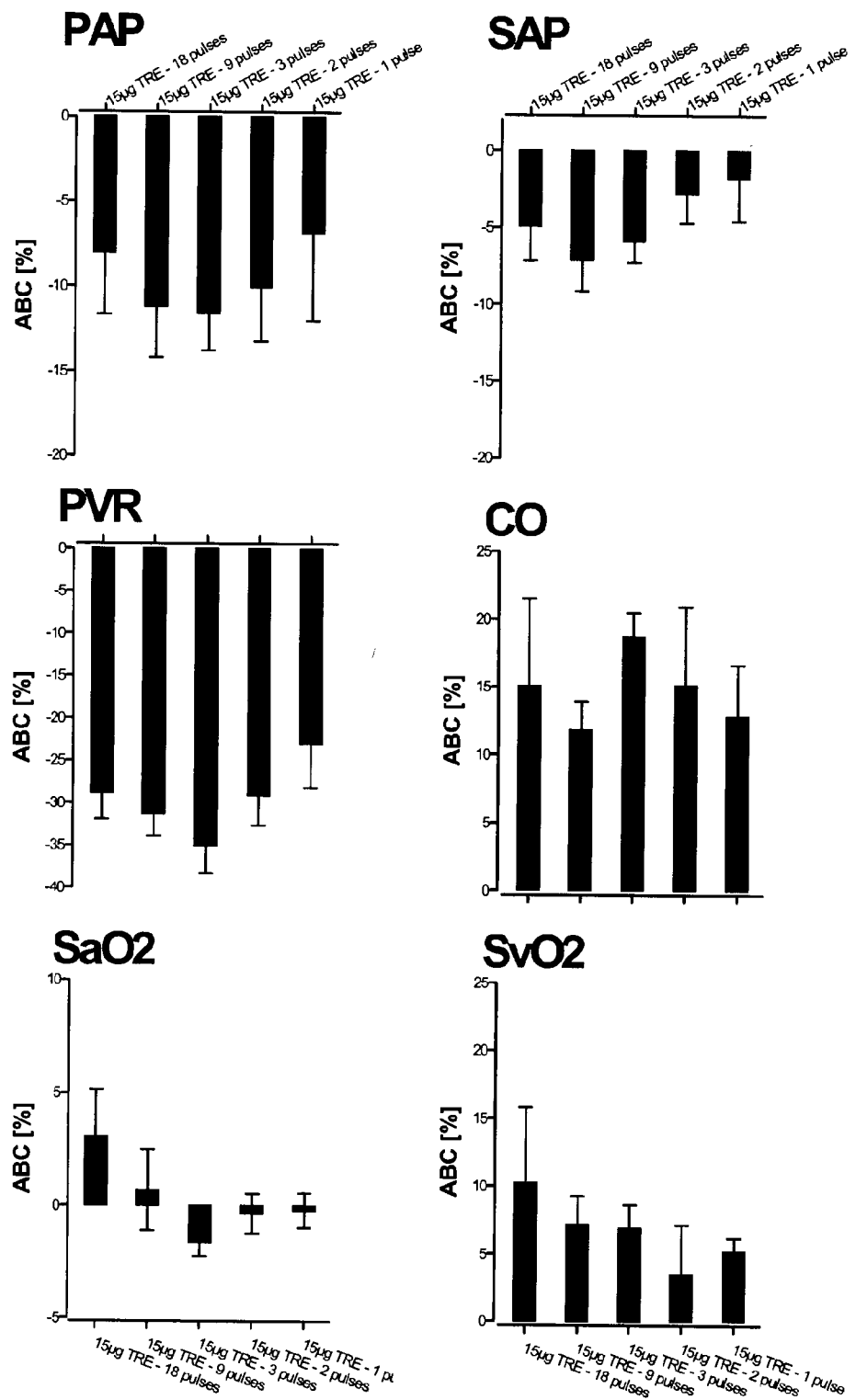
FIG. 11 presents areas between the placebo curve and the responses to 15 µg treprostinil applied at increasing concentrations to minimize inhalation time. Mean±SEM of relative changes of hemodynamic parameters (observation time 120 min). PAP, pulmonary arterial pressure, SAP, systemic arterial pressure, PVR, pulmonary vascular resistance, CO, cardiac output, SaO2, systemic arterial oxygen saturation, SvO2, pulmonary arterial oxygen saturation.

The areas between the curves (ABC) for changes in hemodynamic and gas-exchange parameters after inhalation of 15 µg TRE versus placebo were calculated for an observation time of 120 minutes (FIG. 11). The ABC for both PVR and PAP was comparable between all groups.

Figure 12:
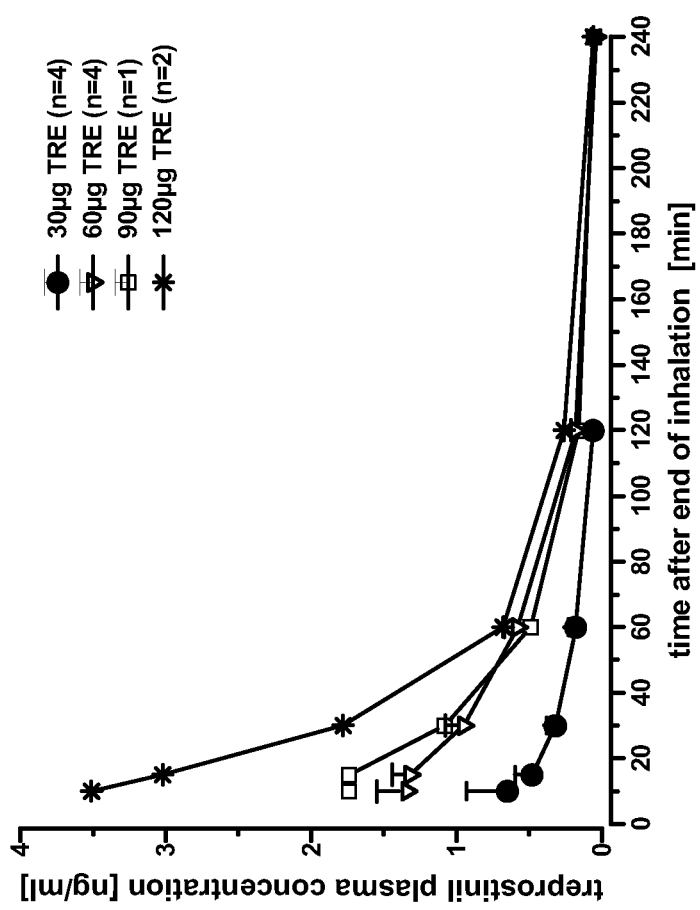
FIG. 12 presents pharmacokinetics of treprostinil after a single inhalation. Treprostinil plasma levels after inhalation of 30 µg, 60 µg, 90 µg or 120 µg treprostinil (6 min inhalation period; experiments correspond to those shown in FIGS. 8 and 9). Data with error bars represent mean values±SEM.

Pharmakokinetic results from study ii): Peak plasma concentrations of treprostinil were found 10-15 minutes after inhalation. Maximal treprostinil plasma concentrations ($C_{max}$) for the 30 µg, 60 µg, 90 µg and 120 µg doses were 0.65±0.28 ng/ml (n=4), 1.59±0.17 ng/ml (n=4), 1.74 ng/ml (n=1) and 3.51±1.04 ng/ml (n=2), respectively (mean±SEM; FIG. 12).

Discussion:

These studies investigated whether i) the acute effects of inhaled treprostinil would be comparable to or possibly advantageous over inhaled iloprost in pulmonary hypertensive patients, ii) the inhaled prostanoid dose might be increased without substantial local or systemic side effects, and iii) if the time of inhalation, which is 6-12 minutes for iloprost, could be reduced significantly by increasing the concentration of treprostinil aerosol.

The patient population in these studies included different forms of precapillary pulmonary hypertension. All these patients had a need for therapy of pulmonary hypertension and reflected the typical population of a pulmonary hypertension center. No major differences in patient characteristics or hemodynamic baseline values existed between the different groups (table 3).

In study i) it was shown that the inhalation of treprostinil and iloprost in similar doses resulted in a comparable maximum pulmonary vasodilatory effect. However, marked differences in the response profile were noted. The onset of the pulmonary vasodilatory effect of inhaled treprostinil was delayed compared to iloprost, but lasted considerably longer, with the PVR decrease continuing beyond the one-hour observation period. Although the average dose of treprostinil was higher than the iloprost dose, no systemic effects were noted after treprostinil inhalation, whereas flush and transient SAP decrease, accompanied by more prominent cardiac output increase, occurred after iloprost inhalation. Such side effects were more prominent than in previous studies with inhaled iloprost. This may have been caused by the fact that the iloprost dose used in this study was 50% higher than the recommended single inhalation dose (5 μg) and that the preceding treprostinil inhalation may have added to the systemic side effects caused by the iloprost inhalation. Surprisingly, with TRE there was no such systemic side effect, although the average effect on PVR was as potent as with iloprost.

This study used a cross-over design in order to minimize the effects of inter-individual differences in response to prostanoids. The short observation period of 1 hour was used to avoid an uncomfortably long catheter investigation. As a study limitation, the short observation interval may have caused carryover effects of the first to the second period as suggested by FIG. 5. However, this still allowed for the interpretation of the study, that both drugs are potent pulmonary vasodilators and that treprostinil effects are significantly sustained compared to the iloprost effects.

The longer duration of action and the virtual absence of side effects (except the bitter taste of treprostinil aerosol, later attributed to metacresol) encouraged increasing the applied treprostinil dose in study ii). Observation time was extended to 3 hours to obtain precise pharmacodynamic data Inhaled treprostinil resulted in a strong pulmonary vasodilation that outlasted the observation time of 3 hours when compared to placebo inhalation. Surprisingly, inhaled treprostinil was tolerated in doses up to 90 μg.

Study iii) successfully demonstrated that the inhalation time could be reduced to literally one single breath of 2000 μg/ml treprostinil solution, thereby applying a dose of 15 μg. This drug administration with a single breath induced pulmonary vasodilation for longer than 3 hours compared to placebo inhalation. Side effects were minor, of low frequency and not related to drug concentration. It was a surprising finding that such high concentrations of treprostinil were so well tolerated.

CONCLUSION

Inhaled treprostinil can be applied in high doses (up to 90 μg) with a minimal inhalation time Inhaled treprostinil exerts high pulmonary selectivity and leads to a long-lasting pulmonary vasodilation.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A kit for treating pulmonary hypertension comprising:
(i) a formulation comprising 200 to 1000 μg/ml treprostinil or a pharmaceutically acceptable salt thereof;
(ii) a pulsed ultrasonic nebulizer comprising an opto-acoustical trigger, configured to
   (a) aerosolize a fixed amount of treprostinil per pulse, and
   (b) deliver by inhalation a therapeutically effective single event dose of said formulation,
said single event dose comprising 15 μg to 90 μg treprostinil or a pharmaceutically acceptable salt thereof delivered in 1 to 18 breaths; and
(iii) instructions for using the pulsed ultrasonic nebulizer with the formulation to treat a patient with pulmonary hypertension by delivering 15 μg to 90 μg treprostinil or a pharmaceutically acceptable salt thereof in 1 to 18 breaths to the patient in the single event dose.

2. The kit of claim 1, wherein the formulation comprises 600 μg/ml of the treprostinil or its pharmaceutically acceptable salt thereof.

3. The kit of claim 1, further comprising instructions for the human not to repeat the single event dose for a period of at least 3 hours.

4. The kit of claim 1, wherein the single event dose produces a peak plasma concentration of treprostinil about 10-15 minutes after the single event dose.

5. The kit of claim 1, wherein the fixed amount of treprostinil or its pharmaceutically salt for each breath inhaled by the human comprises at least 5 ng of treprostinil or its pharmaceutically acceptable salt.

6. The kit of claim 2, wherein the fixed amount of treprostinil or its pharmaceutically salt for each breath inhaled by the human comprises at least 5 ng of treprostinil or its pharmaceutically acceptable salt.

7. The kit of claim 1, wherein the single event dose is inhaled in 3 to 18 breaths by the human.

8. The kit of claim 6, wherein the single event dose is inhaled in 3 to 18 breaths by the human.

9. The kit of claim 6, further comprising instructions for the human not to repeat the single event dose for a period of at least 3 hours.

* * * * *